US010471040B2

(12) United States Patent
Morgan

(10) Patent No.: US 10,471,040 B2
(45) Date of Patent: Nov. 12, 2019

(54) INTRANASAL COMPOSITIONS FOR TREATMENT OF NEUROLOGICAL AND NEURODEGENERATIVE DISEASES AND DISORDERS

(71) Applicant: Lachesis Biosciences Limited, Warrnambool (AU)

(72) Inventor: Timothy Matthias Morgan, Warrnambool (AU)

(73) Assignee: Lachesis Biosciences Limited, Warrnambool (AU)

( * ) Notice: Subject to any disclaimer, the term of this patent is extended or adjusted under 35 U.S.C. 154(b) by 154 days.

(21) Appl. No.: 15/516,233

(22) PCT Filed: Sep. 30, 2015

(86) PCT No.: PCT/AU2015/050591
§ 371 (c)(1),
(2) Date: Mar. 31, 2017

(87) PCT Pub. No.: WO2016/049700
PCT Pub. Date: Apr. 7, 2016

(65) Prior Publication Data
US 2017/0239209 A1 Aug. 24, 2017

(30) Foreign Application Priority Data
Oct. 3, 2014 (AU) ................................ 2014903944

(51) Int. Cl.
| | | |
|---|---|---|
| A61K 31/325 | (2006.01) | |
| A61K 9/00 | (2006.01) | |
| A61K 47/10 | (2017.01) | |
| A61K 47/12 | (2006.01) | |
| A61K 47/32 | (2006.01) | |
| A61K 31/27 | (2006.01) | |
| A61K 9/08 | (2006.01) | |
| A61K 31/439 | (2006.01) | |
| A61K 31/445 | (2006.01) | |
| A61K 31/485 | (2006.01) | |
| A61K 45/06 | (2006.01) | |

(52) U.S. Cl.
CPC .......... *A61K 31/325* (2013.01); *A61K 9/0043* (2013.01); *A61K 9/08* (2013.01); *A61K 31/439* (2013.01); *A61K 31/445* (2013.01); *A61K 31/485* (2013.01); *A61K 45/06* (2013.01); *A61K 47/12* (2013.01); *A61K 47/32* (2013.01)

(58) Field of Classification Search
None
See application file for complete search history.

(56) References Cited

U.S. PATENT DOCUMENTS

| | | |
|---|---|---|
| 3,509,164 A | 4/1970 | Carron et al. |
| 4,806,543 A | 2/1989 | Choi |
| 5,543,421 A | 8/1996 | Benavides et al. |
| 8,710,227 B2 | 4/2014 | Oliver-Shaffer et al. |
| 2003/0225031 A1 | 12/2003 | Quay |
| 2006/0003989 A1 | 1/2006 | Quay et al. |
| 2006/0018839 A1* | 1/2006 | Ieni ..................... A61K 9/0043 424/45 |
| 2008/0020018 A1* | 1/2008 | Moodley ............. A61K 9/5073 424/433 |
| 2009/0047234 A1* | 2/2009 | Touitou ................ A61K 9/0019 424/78.37 |

FOREIGN PATENT DOCUMENTS

| | | |
|---|---|---|
| WO | 2007/043057 A2 | 4/2007 |
| WO | 2007043057 A2 | 4/2007 |
| WO | PCT/AU15/50591 | 9/2015 |

OTHER PUBLICATIONS

Chemical Abstracts Service Registry No. 7732-18-5, accessed May 14, 2018 (Year: 2018).*
Biospace, https://www.biospace.com/article/releases/fda-advisory-committee-recommends-approval-of-novartis-pharmaceuticals-corporation-s-exelon-r-rivastigmine-tartrate-in-the-treatment-of-dementia-as/, May 18, 2006 (accessed May 28, 2019) (Year: 2006).*
Fazil et al. (2012) "Development and evaluation of rivastigmine loaded chitosan nanoparticles for brain targeting," European Journal of Pharmaceutical Sciences. 47:6-15.
Shah et al. (2015) "Nose to brain microemulsion-based drug delivery system of rivastigmine: formulation and ex-vivo characterization," Drug Delivery. 22(7):918-930.
Wavikar et al. (2015) "Rivastigmine-loaded in situ gelling nanostructured lipid carriers for nose to brain delivery," Journal of Liposome Research. 25(2):141-149.
International Search Report corresponding to International Patent Application No. PCT/AU2015/050591, dated Nov. 6, 2015.
Mar. 31, 2017, Morgan, Timothy Matthias.
Araujo et al. (2011) "Cholinesterase inhibitors improve both memory and complex learning in aged beagle dogs," J Alzheimers Dis. 26(1):143-55.
Birks et al. (2009) Rivastigmine for Alzheimer's disease. Cochrane Database of Systematic Reviews. Issue 2. Art No. CD001191. pp. 1-183.
Birks et al. (Mar. 2, 2015) Rivasligmine for Alzheimer's disease. Cochrane Database of Systematic Reviews. Issue 9. Art No. CD001191. pp. 1-198.
Chemuturi et al. (2005) "Comparison of human tracheal/bronchial epithelial cell culture and bovine nasal respiratory explants for nasal drug transport studies," J Pharm Sci. 94(9):1976-85.
Costantino et al. (2007) "Intranasal delivery: physicochemical and therapeutic aspects," Int J Pharm. 337(1-2):1-24.
Costantino et al. (2008) "Intranasal administration of acetylcholinesterase inhibitors," BMC Neurosci. 9(Suppl 3):S6.

(Continued)

*Primary Examiner* — Jeffrey S Lundgren
*Assistant Examiner* — Stephanie K Springer
(74) *Attorney, Agent, or Firm* — Lathrop Gage LLP; Brian C. Trinque; Benjamin A. Vaughan

(57) ABSTRACT

The present invention relates generally to intranasal pharmaceutical compositions. In particular, the present invention is directed to sustained, enhanced delivery of pharmaceutical agents across the nasal mucosa for systemic drug delivery.

8 Claims, 7 Drawing Sheets

(56) References Cited

OTHER PUBLICATIONS

Cutler et al. (1998) "Dose-dependent CSF acetylcholinesterase inhibition by SDZ ENA 713 in Alzheimer's disease," Acta Neurol Scand. 97:244-50.
Davies et al. (1993) "Physiological parameters in laboratory animals and humans," Pharm Res. 10(7):1093-5.
Falck et al. (Jan. 2014) "Metabolism studies of ifenprodil, a potent GluN2B receptor antagonist," J Pharm Biomed Anal. 88:96-105.
Fazil et al. (Aug. 30, 2012) "Development and evaluation of rivastigrnine loaded chitosan nanoparlicles for brain targeting," Eur J Pharm Sci. 47(1):6-15.
Feldman et al. (2007) "Rivastigmine: a placebo controlled trial of twice daily and three times daily regimens in patients with Alzheimer's disease," J Neurol Neurosurg Psychiatry. 78(10):1056-63.
Gobburu et al. (2001) "Pharmacokinetic-pharmacodynamic modeling of rivastigmine, a cholinesterase inhibitor, in patients with Alzheimer's disease," J Clin Pharmacol. 41(10):1082-90.
González-Martínez et al. (Oct. 2013) "Effect of age and severity of cognitive dysfunction on two simple tasks in pet dogs," Vet J. 198(1):176-81.
Gore et al. (1998) "Comparative biomembrane permeation of tacrine using Yucatan minipigs and domestic pigs as the animal model," J Pharm Sci. 87(4):441-7.
Grossberg et al. (2010) "Rivastigmine transdermal system for the treatment of mild to moderate Alzheimer's disease," Int J Clin Pract. 64(5):651-60.
Hossain et al. (2002) "Estimation of the absolute bioavailability of rivastigmine in patients with mild to moderate dementia of the Alzheimer's type," Clin Pharmacokinet. 41(3):225-34.
Hussain et al. (1991) "Intranasal absorption of physostigmine and arecoline," J Pharm Sci. 80(8):750-1.
Imbimbo (2001) "Pharmacodynamic-tolerability relationships of cholinesterase inhibitors for Alzheimer's disease," CNS Drugs. 15:375-90.
Klein et al. (1992) "High-affinity dextromethorphan and (+)-3-(-3-hydroxyphenyl)-N-(1-propyl)piperidine binding sites in rat brain. Allosteric effects of ropizine," J Pharmacol Exp Ther. 260(3):990-9.
Kukanich et al. (2004) "Plasma profile and pharmacokinetics of dextromethorphan after intravenous and oral administration in healthy dogs," J Vet Pharmacol Ther. 27(5):337-41.
Kurz et al. (2009) "Pharmacokinetics of a novel transdermal rivastigmine patch for the treatment of Alzheimer's disease: a review," Int J Clin Pract. 63(5):799-805.
Larner (2010) "Transdermal rivastigmine for Alzheimer's disease: skin deep or scratching the surface?" Int J Clin Pract. 64(5):534-6.
Lefèvre et al. (2008) "Pharmacokinetics and bioavailability of the novel rivastigmine transdermal patch versus rivastigmine oral solution in healthy elderly subjects," J Clin Pharmacol. 48:246-52.
Lefèvre et al. (2008) "Pharmacokinetics and pharmacodynamics of the novel daily rivastigmine transdermal patch compared with twice-daily capsules in Alzheimer's disease patients," Clin Pharmacol Ther. 83:106-14.
Maidment et al. (2006) Cholinesterase inhibitors for Parkinson's disease dementia. Cochrane Database of Systematic Reviews. Issue 1. Art No. CD004747. pp. 1-28.
Mathias et al. (2010) "Non-invasive systemic drug delivery: developabibty considerations for alternate routes of administration," J Pharm Sci. 99(1):1-20.
Merkus et al. (1998) "Nasal mucociliary clearance as a factor in nasal drug delivery," Adv Drug Deliv Rev. 29:13-38.
Miller (2005) "Dextromethorphan psychosis, dependence and physical withdrawal," Addict Biol. 10(4):325-7.
Miller (2011) "Dextromethorphan to dextrorphan: a pathway towards abuse liability," Hum Psychopharmacol. 26(1):89-90.
Moghadamnia et al. (2003) "Physiologically based modelling of inhibition of metabolism and assessment of the relative potency of drug and metabolite: dextromethorphan vs. dextrorphan using quinidine inhibition," Br J Clin Pharmacol. 56(1):57-67.
Mony et al. (2009) "Allosteric modulators of NR2B-containing NMDA receptors: molecular mechanisms and therapeutic potential," Br J Pharmacol. 157(8):1301-17.
Nieoullon et al. (2008) "Importance of circadian rhythmicity in the cholinergic treatment of Alzheimer's disease: focus on galantamine," Curr Med Res Opin. 24(12):3357-67.
Polinsky (1998) "Clinical pharmacology of rivastigmine: a new-generation acetylcholinesterase inhibitor for the treatment of Alzheimer's disease" Clin Ther. 20:634-47.
Posadas et al. (May 2013) "Nicotinic receptors in neurodegeneration," Curr Neuropharmacol. 11(3):298-314.
Quraishi et al. (1997) "The nasal delivery of drugs," Clin Otolaryngol Allied Sci. 22(4):289-301.
Rao et al. (2005) "A stability indicating LC method for rivastigmine hydrogen tartrate," J Pharm Biomed Anal. 37(1):57-63.
Saitoh et al. (1987) "Effects of ifenprodil glucuronide derivative on platelet aggregation and vasocontraction. Jpn J Pharmacol," 44(3):355-7.
Schepmann et al. (2010) "Development of a selective competitive receptor binding assay for the determination of the affinity to NR2B containing NMDA receptors," Pharm Biomed Anal. 53(3):603-8.
Shah et al. (Jan. 27, 2014) "Nose to brain microemulsion-based drug delivery system of rivastigmine: formulation and ex-vivo characterization," Drug Deliv. 22(7):918-30.
Spencer et al. (1998) "Rivastigmine. A review of its use in Alzheimer's disease," Drugs Aging. 13:391-411.
Sweetman: Ed. (2006) Martindale Pharmacopoeia. 35th Ed. p. 1179.2.
Ugwoke et al. (2001) "The biopharmaceutical aspects of nasal mucoadhesive drug delivery," J Pharm Pharmacol. 53(1):3-21.
United States Food and Drug Administration. New Drug Application No. 20-823. Clinical Pharmacology and Biopharmaceutics Review(s): Rivastigmine tartrate capsules. Accessible on the Internet from the main web page: www.fda.gov. [Last Accessed Sep. 14, 2015] 42 pgs.
United States Food and Drug Administration. New Drug Application No. 20-823. Clinical pharmacology and Biopharmaceutics Review(s): Rivastigmine transdermal patch. Accessible on the Internet from the main web page: www.fda.gov. [Last Accessed Sep. 14, 2015] 95 pgs.
Wavikar et al. (Sep. 9, 2014) "Rivastigmine-loaded in situ gelling nanostructured lipid carriers for nose to brain delivery," J Liposome Res. 25(2):141-9.
Williams et al. (1991) "Terpenes and the lipid-protein-partitioning theory of skin penetration enhancement," Pharm Res. 8(1):17-24.
Winblad et al. (2007) "A six-month double-blind, randomized, placebo-controlled study of a transdermal patch in Alzheimer's disease—rivastigmine patch versus capsule," Int J Geriatr Psychiatry. 22:456-67.
Yang et al. (Aug. 16, 2013) "Enhanced brain distribution and pharmacodynamics of rivastigmine by liposomes following intranasal administration," Int J Pharm. 452(1-2):344-54.
Zawertailo (2011) "Author's response to Miller SC: Dextromethorphan to dextrorphan: a pathway towards abuse liability," Hum Psychopharmacol. 26(1):91.
Zawertailo et al. (2010) "Effect of metabolic blockade on the psychoactive effects of dextromethorphan," Hum Psychopharmacol. 25(1):71-9.

* cited by examiner

INTRANASAL COMPOSITIONS FOR TREATMENT OF NEUROLOGICAL AND NEURODEGENERATIVE DISEASES AND DISORDERS

This application is a 35 U.S.C. § 371 filing of International Application No. PCT/AU2015/050591, filed on Sep. 30, 2015, which claims priority to Australian Patent Application No. 2014903944, filed on Oct. 3, 2014, the contents of each of which are incorporated herein by reference in their entirety.

TECHNICAL FIELD

The present invention relates generally to intranasal pharmaceutical compositions. In particular, the present invention is directed to sustained, enhanced delivery of pharmaceutical agents across the nasal mucosa for systemic drug delivery. More particularly, the present invention relates to an intranasal composition comprising rivastigmine for the treatment of neurological and neurodegenerative diseases.

BACKGROUND

Neurological and neurodegenerative diseases and disorders represent potentially debilitating conditions and can affect people of all ages. Neurological and neurodegenerative diseases and disorders may be acquired, congenital, hereditary or sporadic conditions. They are typically associated with widely varying degrees of difficulty which may have significant mental, emotional, physical, and economic consequences for individuals.

Neurodegenerative diseases and disorders are typically characterized by progressive nervous system dysfunction and may be associated with atrophy of the affected central or peripheral structures of the nervous system. Examples of neurodegenerative diseases and disorders include but are not limited to dementia, including Alzheimer's Disease, degenerative nerve diseases, encephalitis, epilepsy, hydrocephalus, stroke, Parkinson's disease, multiple sclerosis, brain cancer, cognitive dysfunction syndrome, amyotrophic lateral sclerosis (ALS), and Huntington's disease.

The term "dementia" is often used to refer to a broad category of brain diseases characterised by a progressive decline in cognition and mental ability wherein memory, thinking, and judgement may be impaired. This type of neurodegenerative disease typically affects those over the age of 60, however early onset forms of the disease are also known. It is estimated that approximately 24 million people worldwide suffer from dementia, of which approximately 50 to 70% are estimated to be due to Alzheimer's disease.

Alzheimer's disease is a highly variable condition which presents and develops differently in each individual. While the cause and progression of the disease is not well understood, there are many common symptoms. In the initial stages, sufferers often exhibit short term memory loss. As the disease progresses, symptoms may include confusion, irritability, aggression, mood swings, trouble with language, and long-term memory loss. The later stages are often characterised by loss of bodily functions which ultimately results to death.

Diagnosis of Alzheimer's disease is usually based on an evaluation of behaviour and cognition, however brain scans and examination of brain tissue is required for a definitive diagnosis. Other neurological and neurodegenerative diseases are also associated with dementia-like symptoms. For example, dementia commonly develops in the advanced stages of Parkinson's disease. Furthermore, cognitive dysfunction syndrome has been recognized as having similarities with Alzheimer's disease.

To date, there is no known cure for dementia or Alzheimer's disease. Current treatments include pharmaceutical and psychosocial treatments, however, no single medication or treatment is known to relieve or reverse the core symptoms of Alzheimer's disease with current treatments typically offering a relatively small symptomatic benefit.

A reduction in the activity of the cholinergic neurons is associated with Alzheimer's disease. Administration of acetylcholinesterase inhibitors may thus be used to increase the concentration of acetylcholine in the brain and counter the loss of acetylcholine caused by the death of cholinergic neurons. Current pharmaceutical treatments for the cognitive symptoms associated with Alzheimer's disease thus include acetylcholinesterase inhibitors and NMDA receptor antagonists.

Rivastigmine, an acetylcholinesterase inhibitor, is currently used for the treatment of patients suffering from neurological conditions, such as dementia caused by Alzheimer's disease and Parkinson's disease (Birks et al. 2009; Birks et al. 2015; Maidment et al. 2006). Furthermore, the use of cholinesterase inhibitors has been shown to help improve cholinergic function associated with other disorders, including cognitive dysfunction syndrome (Gonzalez-Martinez A. et al. 2013; Araujo J A. et al. 2011).

Rivastigmine has the following structure, and may also be provided as a pharmaceutically acceptable salt or hydrate:

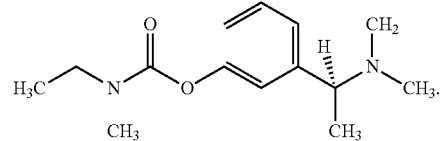

Currently, rivastigmine is available as a capsule or a solution for oral administration and as a transdermal patch. However, the orally available forms of rivastigmine are associated with significant side effects, including nausea, vomiting, diarrhoea and asthenia (Feldman and Lane 2007; Winblad et al. 2007). Additionally, oral rivastigmine has low absolute oral bioavailability of about 35% at a dose of 3 mg, and at higher oral doses of 6 mg and above it exhibits non-linear oral pharmacokinetics (Hossain et al. 2002). The effective treatment of Alzheimer's disease ideally requires central cholinesterase inhibition in order to improve cholinergic signalling in the brain (Cutler et al. 1998; Gobburu et al. 2001). However, greater peripheral cholinesterase inhibition may also occur where higher doses of a given drug are administered to counter low bioavailability, as is the case with oral rivastigmine. This may in turn result in a higher risk of adverse events and associated unwanted side effects.

While the rivastigmine transdermal patch addresses some of these deficiencies, it is known to cause skin irritation in a significant proportion of patients and may also disturb circadian rhythms resulting in disrupted sleep patterns (Lamer 2010; Grossberg et al. 2010; Kurz et al. 2009). Consequently, the treatment discontinuation rate for the transdermal patch was found to be higher than the oral capsule (Winblad et al. 2007).

Accordingly, there is an on-going need to develop new methods of treating neurodegenerative diseases and disorders, such as Alzheimer's disease.

SUMMARY

It has now been surprisingly found that the intranasal delivery of acetylcholinesterase inhibitors, such as rivastigmine, may offer an improved treatment for neurodevelopmental diseases and disorders such as dementia caused by Alzheimer's disease and Parkinson's disease. In particular, intranasal delivery may advantageously provide enhanced delivery of acetylcholinesterase inhibitors such as rivastigmine.

The formulations of the present invention may allow an active agent to be absorbed in a sustained manner providing improved bioavailability at low or reduced doses and/or longer duration of action. Advantageously, the formulations of the present invention may also provide a reduced incidence of side effects when compared with other drug delivery methods.

Accordingly, in one aspect the present invention provides a sustained-release aqueous intranasal formulation comprising rivastigmine or a pharmaceutically acceptable salt thereof, a pH modifying agent and a thickening agent, wherein pH of the formulation is in the range of about 3 to 6.

Intranasal drug delivery offers many advantages including rapid absorption due to abundant capillary vessels, fast onset of action, avoidance of hepatic first-pass metabolism, and utility for chronic medication. Additionally, aqueous intranasal formulations also provide ease of administration, especially administration as an intranasal spray.

The aqueous intranasal formulations comprising rivastigmine or a pharmaceutically acceptable salt thereof, a pH modifying agent and a thickening agent in accordance with the invention may advantageously provide a balance between ease of administration by intranasal delivery and adherence of the formulation to the nasal mucosa. In particular, the aqueous formulations comprising rivastigmine, a pH modifying agent and a thickening agent in accordance with the invention may be administered as a stable intranasal spray yet provide sufficient residence time on the nasal mucosa to allow trans-nasal absorption of the active agent. Furthermore the aqueous intranasal formulations in accordance with the present invention may additionally allow a low or reduced dose of an active agent to be administered, sustained release of the active agent, longer duration of action, and/or a reduced incidence of side effects when compared with other drug delivery methods.

In particular, the pH modifying agent of the intranasal formulations of the present invention may provide or adjust the pH of the formulation to a pH in the range of about 3 to 6. It has surprisingly been found that where the intranasal formulations of the present invention are formulated with a pH range of about 3 to 6, the formulation, in particular the active agent, may exhibit increased pharmaceutical stability. Furthermore, a pH in the range of about 3 to 6 has also been found to assist in solubilising the active agent in solution.

Additionally, the thickening agent of the intranasal formulations of the present invention may modify the viscosity of the formulation to provide improved adherence of the formulation to the nasal mucosa without adversely affecting the ease of administration, in particular administration as an intranasal spray. Without wishing to be bound by theory, the thickening agent may additionally increase the residence time of the formulation on the nasal mucosa, reduce loss of the formulation via mucociliary clearance of the nasal passages and/or improve the trans-nasal absorption. Specifically, in one or more embodiments, the thickening agent may comprise about 0.1% to about 2% by weight of the total composition.

In another aspect, the aqueous intranasal formulations in accordance with the invention may further comprise a sensory agent. The sensory agent in accordance with the present invention may advantageously provide the patient with sensory feedback upon use, for example, that the intranasal formulation of the present invention has been delivered to the correct location within the nasal passage. Furthermore, the sensory agent may also adjust the viscosity in combination with the thickening agent, to further balance the ease of administration of the formulation, in particular as an intranasal spray, with the subsequent adherence of the formulation to the nasal mucosa.

In yet another aspect, the aqueous intranasal formulations in accordance with the invention may advantageously provide an absolute bioavailability equivalent to at least 60% of the active agent, for example, as rivastigmine free base, where bioavailability refers to the fraction of the administered dose of the active agent that reaches the systemic circulation (blood stream).

In a further aspect, the aqueous intranasal formulations in accordance with the invention may further comprise an additional therapeutic agent selected from a sigma-1 receptor agonist, a NMDA antagonist, a nicotinic acetylcholine receptor agonist and combinations thereof. Where the aqueous intranasal formulations of the present invention comprising rivastigmine are administered in combination with an additional therapeutic agent, such a formulation may further reduce or alleviate one or more of the core symptoms of a given neurodegenerative disorder, such as Alzheimer's disease or Parkinson's disease.

In still other aspects, the present invention provides methods of treating neurodegenerative diseases in a mammal, comprising administering an intranasal formulation comprising rivastigmine or a pharmaceutically acceptable salt thereof, a pH modifying agent and a thickening agent, wherein the formulation has a pH in the range of about 3 to 6.

In one or more embodiments, the neurodegenerative disease or disorder may be dementia caused by Alzheimer's disease and Parkinson's disease.

Unless defined otherwise, all technical and scientific terms used herein have the same meanings as commonly understood by one of ordinary skill in the art to which this invention belongs.

The reference to any prior art in this specification is not, and should not be taken as, an acknowledgment or any form of suggestion that that prior art forms part of the common general knowledge.

BRIEF DESCRIPTION OF THE DRAWINGS

FIG. 1: Q Riv across bovine nasal mucosa (0 to 6 h) for Formulation 1 (● round symbols, n=8) and Control Formulation 4 (■ square symbols, n=8) after a finite dose (5 µL/cm$^2$) at 0 h.

FIG. 2: Q Riv across bovine nasal mucosa (0 to 12 h) for Formulation 1 (● round symbols, n=4) and Control Formulation 4 (■ square symbols, n=8) after a finite dose (5 µL/cm$^2$) at 0 h.

FIG. 3: Q Riv across bovine nasal mucosa (0 to 18 h) for Formulation 1 (● round symbols, n=4) and Formulation 2 (■ square symbols, n=4) after repeated finite dosing (5 µL/cm$^2$) at 0 h and 6 h.

FIG. 4: Q Riv across bovine nasal mucosa (0 to 24 h) for Formulation 3 (● round symbols, n=4) after a finite dose (20 µL/cm$^2$) at 0 h.

FIG. 5: Diagram of a flow-through diffusion cell; including nasal mucosal membrane (1); formulation on membrane surface (2); receptor solution inlet (3); receptor solution chamber (4); receptor solution outlet (5); transparent viewing window (6).

DETAILED DESCRIPTION

Figure 1:
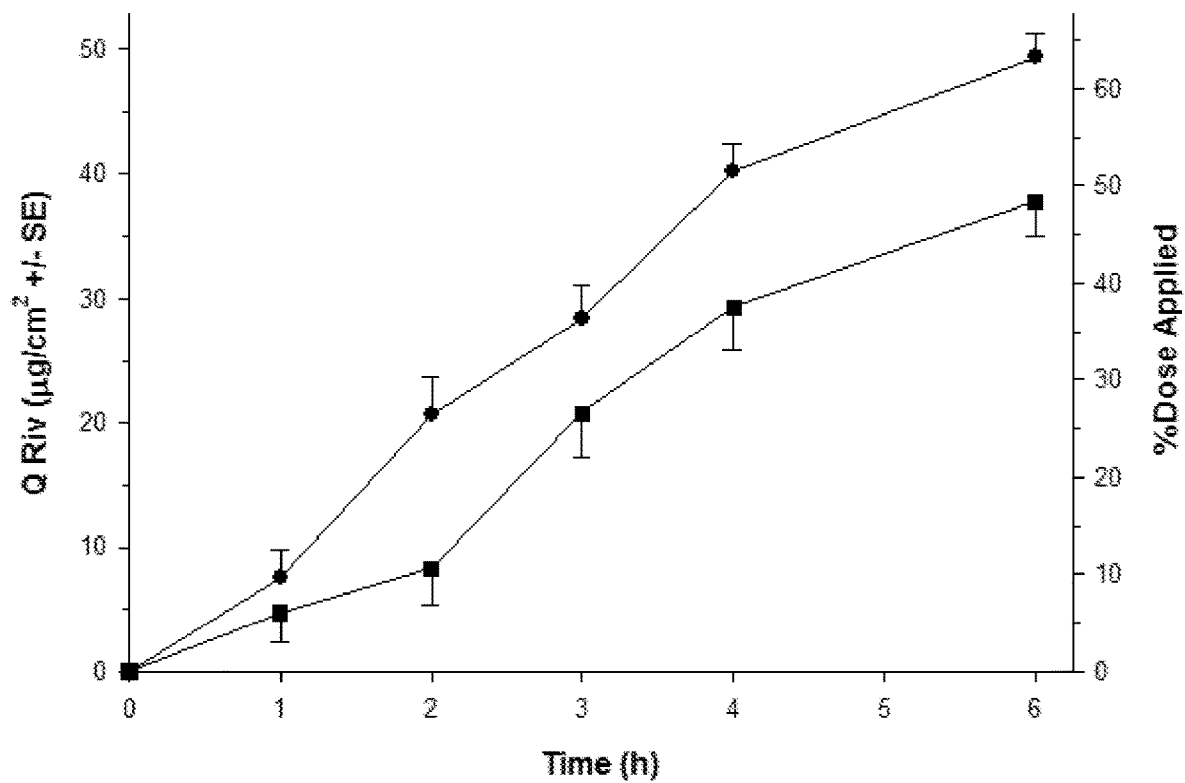
FIGS. 1 to 5 depict various diffusion profiles for nasal formulations applied to freshly excised, adult bovine nasal mucosa held within in vitro, flow-through diffusion cells. The diffusion profiles represent the Cumulative Amount of Rivastigmine as the free base equivalent (Q Riv) over time (h).

The present invention relates to intranasal compositions for treating neurodegenerative diseases or disorders such as dementia associated with Alzheimer's disease. In particular, the present invention relates to intranasal compositions comprising rivastigmine for treating neurodegenerative diseases or disorders.

The present invention also relates to methods of treating neurodegenerative diseases or disorders comprising administering to a mammal in need thereof an effective amount of an intranasal composition as described herein.

The compositions and methods of the present invention are formulated for intranasal delivery. In particular, nasal drug delivery of active agents in accordance with the present invention offers a number of advantages, including but not limited to rapid absorption, fast onset of action, avoidance of hepatic first-pass metabolism, and ease of administration.

More particularly, the compositions and methods of the present invention may advantageously reduce or alleviate one or more of the core symptoms of a given neurodegenerative disorder, for example the symptoms of dementia associated with Alzheimer's diseases or Parkinson's disease. In some aspects, the compositions and methods of the present invention may advantageously enable an active agent to be absorbed in a sustained manner providing improved bioavailability at lower doses and/or longer duration of action. For example, in one or more embodiments, the present invention may provide sustained, enhanced delivery of acetylcholinesterase inhibitors, such as rivastigmine. In certain embodiments, the present invention may provide a reduced incidence of side effects, when compared with current treatments and/or delivery methods.

Preferably the person is in need of such treatment, although the compound may be administered in a prophylactic sense.

References to a "neurodegenerative condition", a "neurodegenerative disorder" or a "neurodegenerative disease", are used interchangeably, and should be understood as a reference to a condition characterised by neurologically based cognitive, emotional and behavioural disturbances.

Neurodegenerative conditions may affect brain or peripheral nerve function. They result from the deterioration of neurons and they are characterised by progressive central or peripheral nervous dysfunction. They are divided into two groups: conditions causing problems with movement or sensation and conditions affecting memory or related to dementia. In one or more embodiments, the neurodegenerative condition is a condition which is associated with modulation of acetylcholinesterase. For example, neurodegenerative conditions in accordance with the invention may include Alzheimer's disease, Alexander disease, Alper's disease, amyotrophic lateral sclerosis, ataxia, telangiectasia, Canavan disease, Cockayne syndrome, corticobasal degeneration, Creutzfeldt-Jakob disease, dementia, Huntington disease, Kennedy's disease, Krabbe disease, Lewy body dementia, Machado-Joseph disease, multiple sclerosis, Parkinson's disease, Pelizaeus-Merzbacher disease, Fronto-Temporal Dementia, Pick's disease, primary lateral sclerosis, Refsum's disease, Sandhoff disease, Schilder's disease, Steele-Richardson-Olszewski disease, tabes dorsalis, Guillain-Barre Syndrome and peripheral neuropathies such as traumatic (nerve severing or crushing), ischemic, metabolic (diabetes, uraemia), infectious, alcoholic, iatrogenic, and genetic neuropathies.

The term "dementia", as used herein would be clear to persons skilled in the art and includes conditions characterised by neurologically-based cognitive, emotional and behavioural impairment, in particular the Diagnostic and Statistical Manual of Mental Disorders IV outlines characterises dementia by the presence of:

Multiple cognitive deficits, including memory impairment and at least one of the following: aphasia, apraxia, agnosia or disturbance in executive functioning; and Impairment of social or occupational function Reference to "characteristic symptoms of dementia" and "characteristic symptoms of Alzheimer's disease" should be understood as a reference to any one or more symptoms which may occur in an individual suffering from dementia, in particular dementia associated with disease such as Alzheimer's disease or Parkinson's disease. These symptoms may be evident throughout the disease course or they may be evident only transiently or periodically. For example, an individual may exhibit severe memory impairment impaired social function in response to specific environmental cues or stressors. It should also be understood that the subject symptoms may not necessarily be exhibited by all individuals suffering from dementia or Alzheimer's disease. For example, some individuals may suffer from cognitive deficits without obvious impairment of social function. However, for the purpose of the present invention, any such symptoms, irrespective of how many or few patients ever actually exhibit the given symptom, are encompassed by this definition. Without limiting the present invention to any one theory or mode of action, the symptoms that are most commonly associated with Alzheimer's disease include cognitive deficits and impaired social or occupational function.

Examples of cognitive deficits and impaired social or occupational function include, but are not limited to:

Forgetfulness, especially of the names of family members, everyday objects appointments or events;

Misplacing items or possessions;

Disorientation and misinterpreting spatial relationships;

Impairment of speech and writing;

Difficulty thinking, concentrating or and reasoning;

Difficulty making routine judgments and decisions;

Difficulty planning and performing familiar tasks; and

Changes in personality and behaviour; including depression, anxiety, social withdrawal, mood swings, distrust, irritability and aggressiveness, changes in sleeping habits, wandering, loss of inhibitions and delusions In addition to the fact that there may be significant variation between dementia and/or Alzheimer's patients in terms of the symptoms they exhibit, it should also be understood that there are other conditions and disorders which are also characterised by one or more of these symptoms. For example similar dementia symptoms, are also commonly observed in patients with Parkinson's disease. Accordingly, reference to a condition characterised by one or more symptoms characteristic of dementia and/or Alzheimer's disease should be understood as a reference to any neurodegenerative condition which is characterised by the presence of one or more of these symptoms.

In one embodiment, said condition is a condition characterised by one or more symptoms of dementia.

In another embodiment, said condition is Alzheimer's disease.

The term "mammal" as used herein includes humans, primates, livestock animals (e.g. horses, cattle, sheep, pigs, donkeys), laboratory test animals (e.g. mice, rats, guinea pigs), companion animals (e.g. dogs, cats) and captive wild animals (e.g. kangaroos, deer, foxes). Preferably, the mammal is a human.

For certain of the abovementioned conditions it is clear that the methods of the invention may be used prophylactically as well as for the alleviation of acute symptoms. References herein to "treatment" or the like may therefore include such prophylactic treatment, as well as therapeutic treatment of acute conditions or symptoms. Accordingly, In one or more embodiments, the present invention provides intranasal compositions for therapeutic treatment of neurodegenerative diseases or disorders. In other embodiments, the present invention provides intranasal compositions for prophylactic treatment of neurodegenerative diseases or disorders.

One of skill in the art will be familiar with the difficulties in administering traditional medications, including lag phases before the effects are observed, and/or systemic dosage concentration peaks and troughs following administration.

The present invention relates to an intranasal composition comprising an acetylcholinesterase inhibitor that may provide sustained, enhanced delivery of the active agent across nasal mucosa over a prolonged period. In particular, intranasal delivery across nasal mucosa in accordance with the invention may advantageously provide sustained, enhanced systemic delivery of rivastigmine and its primary metabolite, 3-[(1 S)-1-(dimethylamino)ethyl]phenol, also referred to as NAP 226-90 (hereafter "NAP 226-90" or "the primary metabolite of rivastigmine").

Accordingly, in one aspect the present invention provides a composition for intranasal delivery comprising an acetylcholinesterase inhibitor. In particular, the composition according to the present invention may be administered for treatment or prevention of neurodegenerative diseases or disorders, such as dementia associated with Alzheimer's disease. Specifically, in one or more embodiments, the present invention provides a composition comprising rivastigmine or a pharmaceutically acceptable salt thereof for intranasal delivery.

It is estimated that the potency of NAP 226-90 is 10 times less than rivastigmine (Gobburu et al. 2001). Kurz et al. (2009) indicated that oral administration of rivastigmine may result in a NAP 226-90 to rivastigmine plasma ratio greater than one. Furthermore, in the case of oral administration of rivastigmine, higher plasma ratios of NAP 226-90 to rivastigmine have been linked to greater and undesirable levels of peripheral anticholinesterase inhibition. As previously described, peripheral cholinesterase inhibition has been associated with increased incidence of adverse events and/or unwanted side effects, such as nausea, vomiting and diarrhoea. Without wishing to be bound by theory, presystemic metabolism due to direct exposure of rivastigmine to the gut wall or by hepatic first-pass metabolism of rivastigmine may be responsible for higher plasma ratios of the metabolite NAP 226-90 to rivastigmine in the case of oral administration. Accordingly, lower plasma ratios of the metabolite NAP 226-90 to rivastigmine are thus desirable.

The intranasal administration of an aqueous solution comprising rivastigmine in accordance with the invention may provide a lower plasma ratio of the metabolite NAP 226-90 to rivastigmine when compared with oral dosing of rivastigmine. In one or more embodiments, intranasal administration in accordance with the present invention may advantageously provide a plasma ratio of NAP 226-90 to rivastigmine of less than about 1.4:1, preferably less than about 1.2:1, more preferably less than about 1:1, still more preferably less than about 0.8:1, most preferably less than about 0.6:1.

It is understood that the active agents in accordance with the present invention may be provided as the free base form or as a pharmaceutically salt or derivative. The term "pharmaceutically acceptable salts" includes pharmaceutically acceptable solvates and hydrates, and pharmaceutically acceptable addition salts of the compounds. Pharmaceutically acceptable derivatives of rivastigmine could be provided in the form of a prodrug, which may, upon administration to a subject, be capable of providing (directly or indirectly) a compound of the present invention or an active metabolite or residue thereof.

In one or more embodiments, the pharmaceutically acceptable salts in accordance with the invention may include acid addition salts, and the salts of quaternary amines and pyridiniums. For use in medicine, the salts of the provided compounds will be pharmaceutically acceptable salts, but it will be appreciated that non-pharmaceutically acceptable salts also fall within the scope of the present invention, since these are useful as intermediates in the preparation of pharmaceutically acceptable salts. A pharmaceutically acceptable salt involves the inclusion of another molecule such as an acetate ion, a succinate ion, a tartrate ion or other counter ion. The counter ion may be any organic or inorganic moiety that stabilizes the charge on the parent compound. Furthermore, a pharmaceutically acceptable salt may have more than one charged atom in its structure. When multiple charged atoms are present in the parent drug, its pharmaceutically acceptable salts will have multiple counter ions and these can be several instances of the same counter ion or different counter ions. Hence, a pharmaceutically acceptable salt can have one or more charged atoms in the parent compound and/or one or more counter ions.

Acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicylic, sulfamic, or tartaric acids. The counter ion of quaternary amines and pyridiniums include chloride, bromide, iodide, sulfate, phosphate, methansulfonate, citrate, acetate, malonate, fumarate, sulfamate, and tartrate. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others. The preparation of the pharmaceutically acceptable salts described above and other typical pharmaceutically acceptable salts is more fully described by Berge et al., "Pharmaceutical Salts," *J. Pharm. Sci.*, 1977: 66:1-19.

In some embodiments, salts of the active agents in accordance with the invention may be prepared from the free form of the compound in a separate synthetic step prior to incorporation into the compositions of the present invention. In still other embodiments, salts of the active agents in accordance with the invention may be prepared in situ during preparation of the composition for administration. For example, the composition for administration may further comprise an appropriate acid which, upon contact with the free form of the active agent, forms a desired pharmaceutical salt in situ for administration.

In one or more embodiments, the compositions for intranasal delivery comprise an acetylcholinesterase inhibitor such as rivastigmine or a pharmaceutically acceptable salt thereof. Where rivastigmine is provided as a pharmaceutically acceptable salt, it may be provided as an acid addition salt. Acid addition salts of rivastigmine in accordance with the invention include hydrochloric, hydrobromic, sulfuric, phosphoric, methanesulfonic, toluenesulphonic, benzenesulphonic, acetic, propionic, ascorbic, citric, malonic, fumaric, maleic, lactic, salicylic, sulfamic, or tartaric acid salts. In particular, rivastigmine in accordance with the invention may be provided as a tartrate salt. In some embodiments, a rivastigmine salt may be prepared from the free form of the compound prior to incorporation into the compositions of the present invention. In still other embodiments, the desired rivastigmine salt may be formed by addition of an appropriate acid to the free form of the compound in situ prior to administration.

As previously described, the present invention encompasses intranasal compositions comprising a desired active agent as the free base form or as a pharmaceutically salt or solvate thereof. Where specific dosages or concentrations of, for example, rivastigmine are referred to herein, it is understood that the specific dosage or concentration refers to the concentration of or equivalent to the free base of rivastigmine. Accordingly, where a pharmaceutically acceptable salt of an active agent is used, for example rivastigmine tartrate, a person skilled in the art would readily understand that the concentrations or dosages in respect of the salt, refers to the equivalent concentration or dosage of the free base form of rivastigmine. In some embodiments, the intranasal pharmaceutical composition comprises an aqueous formulation of rivastigmine or a pharmaceutically acceptable salt wherein the rivastigmine in an amount of about 0.05 to about 20% w/v, about 0.10 to about 15% w/v, about 0.15 to about 6% w/v, about 0.2 to about 5% w/v, about 0.3 to about 3% w/v, about 0.6 to about 2.5% w/v, about 1 to about 2% w/v; about 1.25 to about 1.75% w/v. In still other embodiments, the intranasal pharmaceutical composition comprises an aqueous formulation of rivastigmine or a pharmaceutically acceptable salt wherein the rivastigmine in an amount of about 0.5% to about 15% by weight.

It has surprisingly been found that the specific combination of rivastigmine or a pharmaceutically acceptable salt thereof, a pH modifying agent and a thickening agent in accordance with the invention may advantageously balance the ease of administration by intranasal delivery with the subsequent adherence to the nasal mucosa. In particular, the aqueous formulations comprising rivastigmine, a pH modifying agent and a thickening agent in accordance with the invention may offer improved balance between viscosity, sprayability, absorption, sustained release and/or enhanced bioavailability for effective intranasal administration of active agents. In particular, the specific combination of agents may offer improved trans-nasal absorption and increased residence time on the nasal mucosa to ultimately provide enhanced bioavailability and/or sustained release of the desired active agent without adversely affecting the ease of administration, in particular as an intranasal spray. Furthermore, the judicious selection of agents and components may enable low or reduced doses of an active to be administered, longer duration of action, and/or a reduced incidence of side effects when compared with other drug delivery methods. For example, the specific combination of agents of the formulations comprising rivastigmine in accordance with the invention may advantageously provide a formulation which balances viscosity, sprayability and absorption such that it may be administered intranasally. Furthermore, the specific combination of agents in accordance with the present invention, which provides a formulation that may be administered intranasally, may also advantageously provide improved methods of treating neurodegenerative diseases in a mammal, such as Alzheimer's disease or Parkinson's disease.

The pH modifying agent used in the intranasal formulation of the present invention may be any pharmaceutically acceptable pH-modifying agent which provides or adjusts the pH of the formulation to a pH in the range of about 3 to 6. Where the intranasal formulations of the present invention are formulated with a pH in the range of about 3 to 6, the formulation, in particular the active agent, may advantageously exhibit increased pharmaceutical stability and/or shelf life. For example, it has surprisingly been found that rivastigmine tartrate formulated in an aqueous intranasal spray solution with pH range of about 3 to 6 in accordance with the invention, is pharmaceutically stable over a prolonged time period, such as at least 3 months, preferably at least 6 months, more preferably at least 1 year, even more preferably at least 2 years. Furthermore, formulating intranasal formulations with a pH in the range of about 3 to 6 in accordance with the invention may advantageously assist in solubilising the active agent in solution. Accordingly, the pH modifying agent may be any agent suitable for use and administration in an intranasal formulation which provides or adjusts the pH of the formulation to a pH in the range of about 3 to 6. In one or more embodiments, the pH modifying agent in accordance with the invention may be a buffer. In one or more other embodiments, the pH modifying agent may be any pharmaceutically acceptable acidifying or alkalizing agent that is compatible with the other components of the compositions and which adjusts the pH of the formulation to a pH in the range of about 3 to 6. Suitable pH modifying agents in accordance with the invention include but are not limited to organic acids and their corresponding salts, mineral acids, alkali metal phosphates, carbonates, borates, hydroxides, base and mixtures thereof. In one or more embodiments, the pH modifying agent is selected from lactic acid, citric acid, tartaric acid, phosphoric acid, acetic acid, hydrochloric acid, nitric acid and their corresponding salts, sodium or potassium metaphosphate, sodium or potassium phosphate, sodium or potassium acetate, ammonia, sodium carbonate, sodium or potassium hydroxide, dibasic sodium phosphate, sodium borate, and mixtures thereof. In one or more other embodiments, the pH modifying agent may be a buffer. In particular, a buffer in accordance with the invention may comprise an acid and a salt, such as the corresponding salt of the acid. Suitable buffers include, but are not limited to, citrate, phosphate, acetate and glycinate buffers, wherein the buffer adjusts or maintains the pH of the formulation to a pH in the range of about 3 to 6.

As described above, the pH modifying agent in accordance with the invention may be any agent which provides or adjusts the pH of the formulation to a pH in the range of about 3 to about 6, preferably in the range of about 3 to 5, more preferably about 3 to 4. In other embodiments, the pH modifying agent in accordance with the invention is an agent which provides or adjusts the pH of the formulation to a pH of about 3, about 3.4, about 3.5, about 3.6, about 3.7, about 3.8, about 4, about 4.5, about 5, about 5.5, or about 6. In one or more embodiments, the pH modifying agent is a citrate buffer. In some embodiments, the citrate buffer may comprise citric acid and a citrate salt, such as sodium citrate. In particular, the buffer may comprise from about 0.01% to about 1% by weight of the total composition. In still other embodiments, the pH modifying agent is an organic acid alone, such as citric acid.

The intranasal formulations of the present invention may also comprise a thickening agent. The use of a thickening agent may provide improved adherence of the formulation to the nasal mucosa without adversely affecting the ease of administration, in particular administration as an intranasal spray. Furthermore, the thickening agent may advantageously improve the trans-nasal absorption of the active agent, increase the residence time of the formulation on the nasal mucosa and/or reduce loss of the formulation via mucociliary clearance of the nasal passages. As such, the use of a thickening agent may advantageously provide enhanced bioavailability and/or sustained release of the desired active agent.

In one or more embodiments, the thickening agent in accordance with the invention may be any pharmaceutically acceptable, nasal mucosa-tolerant excipient known to those skilled in the art. The thickening agent in accordance with the invention may advantageously contribute to the controlled release of the active ingredient on the mucosal membranes. Suitable thickening agents in accordance with the invention include methylcellulose, ethylcellulose, hydroxy-ethylcellulose, hydroxyl propyl cellulose, hydroxy propyl methylcellulose, sodium carboxy methylcellulose; polyacrylic acid polymers, poly hydroxyethyl methylacrylate; polyethylene oxide; polyvinyl pyrrolidone; polyvinyl alcohol, tragacanth, sodium alginate, araya gum, guar gum, xanthan gum. lectin, soluble starch, gelatin, pectin and chitosan. In particular, the thickening agent may be polyvinyl pyrrolidone, also referred to as USP povidone or PVP.

In one or more embodiments, the formulations of the present invention may comprise an amount of a thickening agent which improves adherence of the formulation to the nasal mucosa without adversely affecting administration of the formulation as an intranasal spray. Specifically, in one or more embodiments the thickening agent may comprise about 0.1% to about 2% by weight of the total composition, preferably the thickening agent may comprise about 0.25% to about 1.5% by weight of the total composition, more preferably the thickening agent may comprise about 0.5% to about 1% by weight of the total composition.

In one or more embodiments, the intranasal compositions in accordance with the invention may further comprise a sensory agent. The inclusion of a sensory agent may provide the patient with sensory feedback upon use, which allows the patient to recognize that administration has occurred, and may aid the patient's recollection of administration. For example, a sensory agent may provide direct feedback to the patient that the dose has been delivered to the correct location within the nasal passages. In particular, in some aspects the sensory agent may provide mucosal feel, pleasant aroma (smell) and an appealing taste. For example, when a sensory agent is delivered in an intranasal formulation, a small amount of residual formulation may be removed by mucociliary clearance of the nasal passages towards the nasopharynx and eventually swallowed to provide a pleasant taste. The inclusion of a sensory agent may also advantageously provide improved patient compliance and/or a positive psychological effect. Furthermore, in view of the fact that the sensory agent may provide direct feedback to the patient that the dose has been delivered, it advantageously eliminates the need for an 'audible click' within the metered-dose nasal spray device as a means of registering to the patient that a dose has been delivered. For example, a marketed fentanyl intranasal spray for the treatment of break-through pain relies on an audible click device to provide feedback to patients. Simplifying the metered-dose nasal spray device, for example by eliminating the need for an 'audible click', also has the benefit of reducing the cost of manufacture of the nasal spray of this invention as a standard metered-dose nasal spray nozzle, actuator and bottle can be used if desired.

The inclusion of a sensory agent may also enhance the prophylactic or therapeutic effect of compositions of the present invention. For example, the inclusion of a sensory agent may improve the delivery of rivastigmine across the nasal mucosa, assist partitioning into the mucus layer and nasal mucosa to aid absorption and/or aid in the break-up of the spray plume upon actuation of a metered-dose nasal spray nozzle, that is, by increasing and/or maintaining the desired spray plume angle upon actuation. Furthermore, the sensory agent may also adjust the viscosity in combination with the thickening agent, to further balance the ease of administration of the formulation, in particular as an intranasal spray, with the subsequent adherence of the formulation to the nasal mucosa.

In one or more embodiments, the sensory agent in accordance with the invention may be any pharmaceutically acceptable, nasal mucosa-tolerant excipient known to those skilled in the art. In some embodiments, the sensory agent may be selected from coolants, salivating agents, and warming agents. Suitable sensory agents include, but are not limited to, a C2 to C4 alcohol, such as ethanol or isopropanol, menthols, terpenes, thymol, camphor, capsicum, phenol, carveol, menthol glucuronide, eucalyptus oil, benzyl alcohol, salicyl alcohol, clove bud oil, mint, spearmint, peppermint, eucalyptus, lavender, citrus, lemon, lime, hexylresorcinol, ketals, diols, and mixtures thereof. Other suitable mucosa-tolerant terpenes are described in Williams and Barry (2001), incorporated herein by reference.

In one or more embodiments, the aqueous intranasal formulations in accordance with the invention may advantageously provide an absolute bioavailability equivalent to at least 60% of the active agent, for example, rivastigmine free base. The terms "bioavailability" or "bioavailable" as used herein refer generally to the rate and extent of absorption of a given active agent into the systemic circulation and, more specifically, the rate or measurements intended to reflect the rate and extent to which a given active agent becomes available at the site of action or is absorbed from a drug product and becomes available at the site of action. For example, the extent and rate of absorption of a given active agent from a composition for nasal administration of the present invention may be reflected by a time-concentration curve of said active agent in systemic circulation. For measurement and calculation purposes bioavailability means the fraction of the administered dose of the active agent that reaches the systemic circulation (i.e. blood stream). It can range from 0% (no active agent) to 100% (all the administered active agent). Absolute bioavailability is the amount of active agent from a formulation that reaches the systemic circulation relative to an intravenous (IV) dose. The IV dose is assumed to be 100% bioavailable since the active agent is injected directly into the systemic circulation. Absolute bioavailability (F) can be calculated by dividing the $AUC_{0-\infty}$ nasal by the $AUC_{0-\infty}$ IV, where $AUC_{0-\infty}$ is the area under the curve of the blood plasma concentration-time profile of the active agent from zero to infinity hours for an equivalent nasal and IV dose, respectively. Accordingly, in one or more embodiments, the aqueous intranasal formulations in accordance with the invention may advantageously provide an absolute bioavailability equivalent to at least 60% of the active agent, preferably an absolute bioavailability equivalent to at least 65% of the active agent, more preferably an absolute bioavailability equivalent to at least 70% of the active agent, even more preferably an absolute bioavailability equivalent to at least 75% of the active agent, even more preferably an absolute bioavailability equivalent to at least 80% of the active agent, most preferably an absolute bioavailability equivalent to at least 85% of the active agent. Without wishing to be bound by theory, a person skilled in the art would recognise that a degree of variability may exist in the absolute bioavailability of a given drug when administered as an aqueous intranasal formulation in accordance with the invention between individual patients depending on factors including, for example, general health, intrinsic drug clearance rates and the nature of the drug administered. Accordingly, in some embodiments, the intranasal formulations in accordance with the invention may advantageously provide improved individual dosage adjustment within, below and above an effective dosing range, particularly where a degree in variability in bioavailability is observed or required. For example, it is recognised that the intrinsic clearance (CL) of rivastigmine varies up to 4-fold in Alzheimer's disease patients (Hossain et al. 2002). Accordingly, the intranasal formulations described herein advantageously enable flexible individual dosage adjustment as required.

Furthermore, in one or more embodiments the aqueous intranasal formulations in accordance with the invention may advantageously provide an improved dose response, that is, for example with regard to the degree of absorption, the rate of absorption, and/or the duration of action or efficacy. Bioequivalence as used herein is understood to mean that an active agent in two or more alternative dosage forms reach the general circulation at the same relative rate and the same relative extent, that is, the plasma or serum level profile of a given active obtained by administration of the two alternative dosage forms are substantially similar. Furthermore, a person skilled in the art would recognise that the relative rate and degree of absorption of a given active may be characterised by a range of measures, including for example, the maximum plasma concentration ($C_{max}$), time to maximum plasma concentration ($T_{max}$), therapeutic plasma concentration ($C_{ther}$), average plasma concentration ($C_{avg}$) and/or the length of time therapeutic plasma concentration is maintained ($T_{maint}$) following administration of a given dose.

In one or more embodiments the aqueous intranasal formulations in accordance with the present invention may provide a maximum therapeutic rivastigmine plasma concentration ($C_{max}$) of at least about 3000 pg/mL, preferably about 4000 pg/mL. more preferably about 5000 pg/mL. Additionally, in one or more further embodiments, the time to maximum rivastigmine plasma concentration ($T_{max}$) is less than 3 hours, more preferably less than 2 hours, even more preferably less than 1.5 hours, even more preferably less than 1.25 hours following administration of an initial dose at time equals zero hours. Furthermore, in one or more other embodiments, the aqueous intranasal formulations in accordance with the present invention may provide a therapeutic rivastigmine plasma concentration ($C_{ther}$) in the range of about 2000 pg/mL to about 20,000 pg/mL, preferably about 2500 pg/mL to about 15,000 pg/mL, more preferably about 3500 pg/mL to about 10,000 pg/mL, even more preferably about 4000 pg/mL to about 8,000 pg/mL. In one or more other embodiments, the aqueous intranasal formulations in accordance with the present invention may provide an average plasma concentration ($C_{avg}$) in the range of about 500 pg/mL to about 20,000 pg/mL, where $C_{avg}$ is calculated from the AUC over a given time interval ($AUC_{0-6h}$) divided by the prospective dosage interval. Additionally, in one or more further embodiments, the therapeutic rivastigmine plasma concentration ($C_{ther}$) in the range of about 2000 pg/mL to about 20,000 pg/mL may be maintained ($T_{maint}$) for a period of at least 4 hours, preferably at least 4.5 hours, more preferably at least 5 hours, even more preferably at least 5.5 hours, even more preferably 6 hours following administration of an initial dose at time equals zero hours. It would be understood by a person skilled in the art that the therapeutic rivastigmine plasma concentration ($C_{ther}$) could be maintained ($T_{maint}$) for an even longer period, for example at least 8 hours, preferably at least 10 hours, more preferably at least 12 hours where a repeat dose is subsequently administered. For example, a therapeutic rivastigmine plasma concentration ($C_{ther}$) could be maintained ($T_{maint}$) for a period of 12 hours where a repeat dose is administered at least 4 hours, preferably at least 4.5 hours, more preferably at least 5 hours, even more preferably at least 5.5 hours, even more preferably 6 hours after the first dose is administered. In still further embodiments, the therapeutic rivastigmine plasma concentration ($C_{ther}$) in the range of about 2000 pg/mL to about 20,000 pg/mL may be maintained ($T_{maint}$) for waking hours. Advantageously, an intranasal formulation having a $C_{max}$, a $C_{avg}$, a $C_{ther}$, a $T_{max}$ and/or a $T_{maint}$ as described may alleviate or treat one or more of the symptoms associated with a given neurodegenerative disorder, such as Alzheimer's disease. In still other embodiments, a $C_{max}$, a $C_{avg}$, a $C_{ther}$, a $T_{max}$, and/or a $L_{maint}$ as described may provide a sustained-release treatment for a given neurodegenerative disorder, such as Alzheimer's disease. In one or more embodiments, the absolute bioavailability (F) and $T_{maint}$ may advantageously be maximised whilst minimising the $C_{max}$ to $C_{ther}$ ratio.

In some embodiments, the intranasal compositions in accordance with the present invention may further comprise an antioxidant, surfactant, co-solvent, adhesive, stabilizer, osmolarity adjusting agent, preservative, penetration enhancer, chelating agent, sweetening agent, flavoring agent, taste masking agent, or colorant. Furthermore, some agents or components of the intranasal formulations in accordance with the invention may concurrently act, for example, as both a pH modifying agent and an osmolarity adjusting agent or as both sensory agent and a co-solvent. For example, where ethanol is used as a sensory agent in accordance with the invention, it may further function as a penetration enhancer and/or a cosolvent. Where a given agent or component of an intranasal formulation is described herein with respect to a particular function, it is in no way taken to be limited to a single function only. It would be understood by a person skilled in the art that agents or components may additionally perform alternative or multiple functions.

Where the intranasal compositions in accordance with the invention comprise a co-solvent, the co-solvent may be any pharmaceutically acceptable co-solvent. Co-solvents in accordance with the present invention may include but are not limited to alcohols, polyvinyl alcohols, propylene glycol, polyethylene glycols and derivatives thereof, glycerol, sorbitol, polysorbates, ethanol, and mixtures thereof. In particular, the co-solvent in accordance with the present invention is selected from glycerol, propylene glycol and mixtures thereof. In still other embodiments, the co-solvent may comprise from about 1% to about 60% by volume of the total composition, preferably from about 2 to about 50%, more preferably from about 3 to about 40%, even more preferably from about 5 to about 35% by volume of the total composition. In some embodiments, the sensory agent in accordance with the invention may, for example, additionally act as a co-solvent or a penetration enhancer.

Where the intranasal compositions in accordance with the invention comprise a preservative, the preservative may be selected from any pharmaceutically acceptable preservative. In one or more embodiments, the preservative may be selected from benzalkonium chloride, methylparaben, ethylparaben, propylparaben, butylparaben, benzyl alcohol, sodium benzoate, phenylethyl alcohol, and benzethonium. More particularly, the preservative may include benzyl alcohol or sodium benzoate. In one or more embodiments, the preservative may comprise from about 0.1% to about 5% by weight of the total composition, preferably from about 0.2 to about 3% by weight, more preferably from about 0.3% to about 1% by weight of the total composition. In still other embodiments, the intranasal compositions in accordance with the invention do not contain a preservative.

In certain embodiments, it is envisaged that the intranasal compositions comprising rivastigmine described herein may be administered to a person in need thereof as a substitute or replacement for other traditional medication. In other embodiments, it is envisaged that intranasal compositions comprising rivastigmine in accordance with the invention may be administered to a subject in need thereof as a supplement or adjunct to traditional medication. In still other embodiments, it is envisaged that intranasal compositions comprising rivastigmine in accordance with the invention may be administered to a person in need thereof in the absence of adjunct therapy. In still other embodiments, it is envisaged that that intranasal compositions comprising rivastigmine in accordance with the invention may be administered to a person in need thereof in conjunction with, or as an adjunct to, behavioural or cognitive therapies.

Replacing traditional medication with an intranasal composition comprising rivastigmine in accordance with the invention may be advantageous, particularly where the traditional medication is associated with one or more adverse effects (for example, nausea, vomiting, diarrhoea). Examples of medication would be known to those skilled in the art and include, but are not limited to, orally available systemic medications comprising rivastigmine and transdermal patches comprising rivastigmine.

In other embodiments, the intranasal compositions comprising rivastigmine in accordance with the invention may be administered to a subject in need thereof, together with other medication for a discrete period of time, to address specific symptoms. In still other embodiments, the person in need thereof may be treated with both an intranasal composition comprising rivastigmine and one or more additional medications (administered sequentially or in combination) for the duration of the treatment period. Such combination therapy may be particularly useful, for example, where an additive or synergistic therapeutic effect is desired.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of condition, or the amelioration of one or more symptoms (e.g., one or more discernable symptoms) of said condition (i.e., "managing" without "curing" the condition), resulting from the administration of one or more therapies (e.g., one or more therapeutic agents such as a compound or composition of the invention). In specific embodiments, the terms "treat"; "treatment" and "treating" refer to the amelioration of at least one measurable physical parameter of a condition described herein. In other embodiments the terms "treat", "treatment" and "treating" refer to the inhibition of the progression of a condition described herein, either physically by, e.g., stabilization of a discernable symptom or physiologically by, e.g., stabilization of a physical parameter, or both.

The terms "preventing" and "prophylaxis" as used herein refer to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. As used in a standard text in the field, the Physician's Desk Reference, the terms "prevent", "preventing" and "prevention" with regard to a disorder or disease, refer to averting the cause, effects, symptoms or progression of a disease or disorder prior to the disease or disorder fully manifesting itself.

The terms "therapeutic equivalence" or "therapeutically equivalent" as used herein refer to compositions for nasal administration which will produce the same clinical effect and safety profile and/or are pharmaceutical equivalents to other systemic treatments such as orally available compositions. For example, a therapeutic equivalent intranasal composition comprising rivastigmine may provide substantially the same efficacy and toxicity at a lower dosage strength than other systemic treatments such as orally available compositions.

The intranasal compositions of the present invention are administered to the person in need thereof in a treatment effective amount. In some embodiments, a treatment effective amount is a therapeutically effective amount or a prophylactically effective amount. The term "therapeutically effective amount" as used herein means that amount of an active compound, such as an acetylcholinesterase inhibitor including rivastigmine, or pharmaceutical agent sufficient to treat or alleviate the symptoms associated with a given neurodegenerative disorder, such as dementia caused by Alzheimer's disease. The therapeutically effective amount of the compound to be administered will be governed by such considerations, and is either, an incremental maximum tolerated dose, or the minimum amount, necessary to ameliorate, cure, or treat the disease or disorder or one or more of its symptoms. The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease or symptom) and secondary prophylaxis (whereby the disease or symptom has already developed and the patient is protected against worsening of this process).

As used herein, the term "effective amount" relates to an amount of compound which, when administered according to a desired dosing regimen, provides the desired therapeutic activity. Suitable dosages lie within the range of about 0.1 ng per kg of body weight to 100 g per kg of body weight per dosage. The dosage may be in the range of 1 μg to 10 g per kg of body weight per dosage, such as is in the range of 1 mg to 1000 mg per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 200 mg per kg of body weight per dosage, such as up to 50 mg per kg body weight per dosage.

Dosing may occur at intervals of minutes, hours, days, weeks, months or years or continuously over any one of these periods. Suitable dosage intervals include 24 hours, 12 hours, 8 hours, 6 hours, 4 hours, 3 hours, 2 hours, 1 hour, 30 minutes, or 15 minutes. In particular, the intranasal compositions according to the present invention may be administered at an interval of 12 hours, 8 hours, 6 hours or four hours. In still other embodiments, dosing may occur during waking hours or sleeping hours only. Where dosing occurs in waking hours, for example, the administered amount may be an amount sufficient to treat or alleviate the symptoms associated with a given neurodegenerative disorder, such as dementia caused by Alzheimer's disease. Where the active agent is associated with one or more side effects, dosing may occur at intervals sufficient to treat or alleviate the symptoms of a given disease or disorder and concurrently minimise or reduce the associated side effects. In one or more embodiments, where the active agent to be administered is rivastigmine or a pharmaceutically acceptable salt thereof for the treatment of dementia caused by Alzheimer's disease, dosing may advantageously occur during waking hours only to reduce side effects such as disrupted sleep patterns. Disrupted sleep patterns have been associated with administration of existing rivastigmine transdermal patches for a continuous period of 24 hours which necessarily includes sleeping hours. In one or more embodiments, intranasal formulations in accordance with the present invention may provide adjustable, individualised dosing, in particular dosing during waking hours, which may advantageously minimise undesirable cholinergic burden and sleep disturbances whilst delivering an effective dose for the treatment of dementia associated with Alzheimer's and Parkinson's disease.

The terms "administer", "administering" or "administration" in reference to a compound, composition or formulation of the invention means introducing active agent into the system of the animal in need of treatment. When the active agent in accordance with the invention is provided in combination with one or more other active agents, "administration" and its variants are each understood to include concurrent and/or sequential introduction of the compound and the other active agents.

In certain embodiments, an effective amount of a compound for administration one or more times a day to a 70 kg adult human may comprise about 0.0001 mg to about 4000 mg, about 0.0001 mg to about 3000 mg, about 0.0001 mg to about 200 mg, about 0.001 mg to about 1500 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of an extract or compound per unit dosage form.

In certain embodiments, the intranasal compositions of the invention may be at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg, of subject body weight per day, one or more times a day, to obtain the desired therapeutic effect.

Suitable dosage amounts and dosing regimens can be determined by the attending physician and may depend on the particular condition being treated, the severity of the condition as well as the general age, health and weight of the subject. It will be appreciated that dose ranges as described herein provide guidance for the administration of provided pharmaceutical compositions to an adult. The amount to be administered to can be determined by a medical practitioner or person skilled in the art.

The intranasal compositions of the present invention may be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agent, an "effective amount" of the second agent will depend on the type of drug used. Suitable dosages are known for approved agents and can be adjusted by a person skilled in the art according to the condition of the subject, the type of condition(s) being treated and the amount of a compound, extract or composition being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

The phrase "combination therapy" as used herein, is understood to refer to administration of an effective amount, using a first amount of for example rivastigmine or a pharmaceutically acceptable salt thereof as described herein, and a second amount of an additional suitable therapeutic agent.

In certain embodiments, rivastigmine or a pharmaceutically acceptable salt thereof, and the additional therapeutic agent, are each administered in an effective amount (i.e., each in an amount which would be therapeutically effective if administered alone). In other embodiments, rivastigmine or a pharmaceutically acceptable salt thereof, and the additional therapeutic agent are each administered in an amount which alone does not provide a therapeutic effect (a subtherapeutic dose). In yet other embodiments, rivastigmine or a pharmaceutically acceptable salt thereof, can be administered in an effective amount, while the additional therapeutic agent is administered in a sub-therapeutic dose. In still other embodiments, rivastigmine or a pharmaceutically acceptable salt thereof, can be administered in a sub-therapeutic dose, while the additional therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a person in need thereof.

Co-administration encompasses administration of the first and second amounts of therapeutic compounds in an essentially simultaneous manner, such as in a single pharmaceutical composition, for example, an intranasal spray having a fixed ratio of first and second amounts. In addition, such co-administration also encompasses use of each compound in a sequential manner in either order. When co-administration involves the separate administration of the first amount of rivastigmine or a pharmaceutically acceptable salt thereof, and a second amount of an additional therapeutic agent, they are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life, and kinetic profile. For example, rivastigmine or a pharmaceutically acceptable salt thereof, and the second therapeutic agent can be administered in any order within about 24 hours of each other, within about 16 hours of each other, within about 8 hours of each other, within about 4 hours of each other, within about 1 hour of each other, within about 30 minutes of each other, within about 15 minutes of each other, within about 10 minutes of each other or within about 5 minutes of each other.

In one or more embodiments where the rivastigmine or a pharmaceutically acceptable salt thereof is administered with additional therapeutic agent, the agent may be any therapeutic agent which provides a desired treatment outcome. In particular, the additional therapeutic agent may be selected from a sigma-1 receptor agonist, an NMDA antagonist, an nicotinic acetylcholine receptor agonist and combinations thereof. In particular, sigma-1 receptor agonists in accordance with the present invention may include dextromethorphan or pharmaceutically acceptable derivatives thereof, including dextromethorphan hydrobromide; NMDA antagonists in accordance with the present invention may include memantine, ifenprodil, or pharmaceutically acceptable derivatives thereof, including memantine hydrochloride and ifenprodil tartrate; nicotinic acetylcholine receptor agonists in accordance with the present invention may include encenicline or pharmaceutically acceptable derivatives thereof, including encenicline hydrochloride.

Sigma-1 receptor agonists have been recognised to alleviate cognitive deficits and reduce neuronal damage and are thus considered useful agents in the treatment of Alzheimer's disease. U.S. Pat. No. 4,806,543 describes the use of dextromethorphan as a neuroprotective agent in the treatment of Alzheimer's disease and other neurodegenerative disorders, however its practical use as an oral dose form has been limited by both its extensive first-pass metabolism to dextrorphan which can have adverse psychoactive effects (Moghadamnia A A., et al. 2003, Zawertailo L A., et al. 2010; Miller S C., 2011). Furthermore, at high doses, oral dextromethorphan presents an abuse liability risk (Miller S C. 2005). While the addition of oral quinidine with oral dextromethorphan has been known to reduce the first-pass metabolism to dextrorphan, it has the added disadvantage of increasing the risk of cardiac adverse events (Zawertailo L A., et al. 2010, Zawertailo L A. 2011). Accordingly, in some aspects the present invention provides a composition and use of dextromethorphan in combination with rivastigmine, via simultaneous, sequential or separate intranasal administration. Systemic delivery of dextromethorphan in combination with rivastigmine via intranasal administration may advantageously reduce or alleviate one or more of the core symptoms of a given neurodegenerative disorder, for example the symptoms associated with Alzheimer's diseases or Parkinson's disease.

NMDA antagonists are a class of compounds which inhibit the action on the N-Methyl-D-aspartate receptor. The N-Methyl-D-aspartate receptor is recognised to play a role in the glutamatergic system via the NR2B sub-unit and, as a target, is thought to offer an alterative approach to treatment of neurodegenerative diseases such as Alzheimer's or Parkinson's diseases. NMDA antagonists typically induce a state called dissociative anesthesia. Suitable NMDA antagonists in accordance with the present invention may include memantine, ifenprodil, or pharmaceutically acceptable derivatives thereof, such as memantine hydrochloride and ifenprodil tartrate. Memantine has been recognised to alleviate symptoms associated with moderate-to-severe Alzheimer's disease and is also thought to have activity as a non-competitive antagonist at acetylcholine receptors (nAChRs). Ifenprodil has been shown to exhibit activity at the NR2B subunit of the NMDA receptor (Schepmann D., et al. 2010) and may thus alleviate symptoms associated with neurodegenerative diseases such as Alzheimer's disease. U.S. Pat. No. 5,543,421 describes the use of ifenprodil for treating central neurodegenerative diseases in a patient with a dose as low as 1 mg a day. Suitable ifenprodil salts, including neutral tartrate and acid tartrate, have been originally described in U.S. Pat. No. 3,509,164. Without wishing to be bound by theory, it is considered that concerns regarding a lack of selectivity with regard to NMDA antagonists such as ifenprodil may be avoided with low-dose systemic therapy, such as intranasal delivery (Mony L., et al. 2009). Accordingly, in some aspects the present invention provides a composition and use of an NMDA antagonist in combination with rivastigmine, via simultaneous, sequential or separate intranasal administration. Systemic delivery of NMDA antagonists, including memantine, ifenprodil, or pharmaceutically acceptable derivatives thereof, such as memantine hydrochloride and ifenprodil tartrate, in combination with rivastigmine via intranasal administration may advantageously reduce or alleviate one or more of the core symptoms of a given neurodegenerative disorder, for example the symptoms associated with Alzheimer's diseases or Parkinson's disease.

Nicotinic acetylcholine receptor agonists are a class of compounds that bind to nicotinic acetylcholine receptors in the central nervous system, the peripheral nervous systems, skeletal muscles and combinations thereof. Nicotinic acetylcholine receptor agonists are considered to be suitable candidates for treatment of central nervous system disorders, including Alzheimer's disease, Parkinson's disease, schizophrenia, and attention-deficit hyperactivity disorder. Specifically, the use of nicotinic acetylcholine receptor agonists, in particular alpha-7 nicotinic acetylcholine receptor agonists, is considered to improve cognitive function in patients with Alzheimer's disease (Posadas I., et al. 2013). Suitable nicotinic acetylcholine receptor agonists in accordance with the present invention include encenicline or pharmaceutically acceptable derivatives thereof, including encenicline hydrochloride. The intranasal delivery of nicotinic acetylcholine receptor agonists has been described in U.S. Pat. No. 8,710,227, the contents of which is incorporated herein by reference. Accordingly, in some aspects the present invention provides a composition and use of a nicotinic acetylcholine receptor agonist in combination with rivastigmine, via simultaneous, sequential or separate intranasal administration. Systemic delivery of nicotinic acetylcholine receptor agonists, including encenicline or pharmaceutically acceptable derivatives thereof, such as encenicline hydrochloride, in combination with rivastigmine via intranasal administration may advantageously reduce or alleviate one or more of the core symptoms of a given neurodegenerative disorder, for example the symptoms associated with Alzheimer's diseases or Parkinson's disease.

Where rivastigmine is administered in combination with an additional therapeutic agent, the second agent may be administered in any "effective amount" which provides the desired therapeutic activity, as described above. Suitable dosage amounts and dosing regimens of the additional therapeutic agent can be determined by the attending physician and may depend on the particular condition being treated, the severity of the condition as well as the general age, health and weight of the subject. It will be appreciated that dose ranges as described herein provide guidance for the administration of provided pharmaceutical compositions to an adult. The amount to be administered to can be determined by a medical practitioner or person skilled in the art.

For example, suitable systemic doses of dextromethorphan to be used in combination with rivastigmine may be arrived at based on the potency of dextromethorphan as a sigma one receptor agonist. Specifically, dextromethorphan is recognised as having a dissociation constant ($K_d$) of 20 nM in binding studies with rat brain (Klein and Musacchio 1992), equivalent to about 5.4 ng/mL of dextromethorphan. Additionally, the physicochemical properties of dextromethorphan advantageously enable it to readily cross the blood-brain barrier. Assuming an average target plasma concentration of about 5.4 ng/mL and a systemic clearance of about 23 mL/min/kg for example (Kukanich and Papich 2004; Davies and Morris 1993), an effective systemic dose of dextromethorphan as the free base may be in the range of about 1 to about 25 mg per day, preferably about 3 to about 20 mg per day, more preferably about 5 to about 18 mg per day, in particular about 10 to about 15 mg per day, for example, about 12 mg per day.

Accordingly, in one or more embodiments the present invention provides an intranasal composition comprising rivastigmine and dextromethorphan, or a pharmaceutically acceptable salt thereof, including dextromethorphan hydrobromide, wherein the dextromethorphan is in an amount of from about 0.5 to about 15% by weight of the total composition, preferably from about 1 to about 10% by weight of the total composition, more preferably from about 1 to about 7% by weight of the total composition, in particular from about 2 to about 5% by weight of the total composition.

In one or more other embodiments, the present invention provides an intranasal composition comprising rivastigmine and encenicline, or a pharmaceutically acceptable salt thereof, including encenicline hydrochloride, wherein the encenicline is in an amount of from about 0.25 to about 7% by weight of the total composition, preferably from about 0.5 to about 4% by weight of the total composition, more preferably from about 1 to about 3% by weight of the total composition.

With regard to ifenprodil, its use as a low-dose oral dosage formulation is limited by its extensive first-pass metabolism and associated vasodilator effect at higher doses such as, 40 to 60 mg orally daily, or 15 mg i.v. daily, when treating peripheral vascular disease (Falck E. et al. 2014; Saitoh K. et al. 1987, Martindale $35^{th}$ Ed. p1179.2). The intranasal delivery of ifenprodil may advantageously address one or more of these deficiencies. Accordingly, in one or more further embodiments, the present invention provides an intranasal composition comprising rivastigmine and ifenprodil, or a pharmaceutically acceptable salt thereof, including ifenprodil tartrate, wherein the ifenprodil is in an amount of from about 0.001 to about 5% by weight of the total composition, preferably from about 0.005 to about 2% by weight of the total composition, more preferably from about 0.01 to about 1% by weight of the total composition, in particular from about 0.1 to about 0.5% by weight of the total composition.

Furthermore the intranasal delivery of dextromethorphan in combination with rivastigmine, may provide improved bioavailability when compared with oral delivery of dextromethorphan alone (Moghadamnia A A., et al. 2003).

The intranasal compositions of the present invention may be administered in a single dose or a series of doses. While it is possible for the composition to be administered alone, in some embodiments it may be preferable to present it as a pharmaceutical formulation.

In one or more embodiments, the intranasal compositions according to the present invention may be prepared as pharmaceutically acceptable emulsions, microemulsions, solutions, or suspensions In particular, the compositions of the present invention may be prepared as aqueous solutions or suspensions. In one or more embodiments, the present invention provides an aqueous solution comprising rivastigmine for intranasal administration. Where the formulations of the present invention are aqueous solutions or suspensions, the formulations may comprise water is in an amount of greater than 50% by weight of the total composition, preferably greater than about 60% by weight of the total composition, more preferably greater than about 70% by weight of the total composition, even more preferably greater than about 80% by weight of the total composition. In still other embodiments, where the formulations of the present invention are aqueous solutions or suspensions, the formulations may comprise water in the range of from about 80% to about 99% by weight of the total composition, more preferably from about 85% to about 98% by weight of the total composition.

In addition to the active ingredients, the liquid dosage forms may comprise inert diluents commonly used in the art such as, for example, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the intranasal compositions may include adjuvants such as wetting agents, emulsifying and suspending agents, sweetening, flavoring, and perfuming agents. It is recognised that the additional inert diluents may also act as, for example, penetration enhancers, thickening agents, or co-solvents within the scope of the present invention, as previously described.

Where a carrier is used, the carrier must be pharmaceutically "acceptable" in the sense of being compatible with the other ingredients of the composition and not injurious to the subject.

General considerations in formulation and/or manufacture of pharmaceutical intranasal compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Pharmaceutical compositions for intranasal administration in accordance with the invention can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single-or multi-dose unit.

As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The formulations in accordance with the invention may be administered to a person in need thereof by any suitable intranasal delivery methods. Suitable methods for intranasal administration would be well-known to a person skilled in the art. The intranasal compositions disclosed herein can be administered as a spray or drop. Accordingly, suitable commercial packages containing the intranasal formulation can be in any spray container known in the art. In one or more embodiments, the formulations in accordance with the invention may be administered via a spray device or container. Spray devices in accordance with the invention may be single unit dose systems or multiple dose systems, for example comprising a bottle, a pump and/or an actuator. Such spray devices are available commercially. Suitable commercial spray devices include those available from Nemera, Aptar, Bespak and Becton-Dickinson. In still other embodiments, the formulations in accordance with the invention may be administered via an electrostatic spray device, such as described in U.S. Pat. No. 5,655,517. Other suitable means for administering formulations intranasally in accordance with the invention include via a dropper, a syringe, a squeeze bottle, and any other means known in the art for applying liquids to the nasal mucosa in an accurate and repeatable fashion.

The spray devices used to administer the composition can range from single-use metered-dose spray devices, multiple-use metered dose nasal spray devices and are not limited to spraying the solutions into each naris but can be administered as a gentle liquid stream from a plunger, syringe or the like or as drops from a unit-dose or multi-dose squeeze bottle, or other means known in the art for applying liquids to the nasal mucosa in an accurate and repeatable fashion.

In one or more embodiments, a spray device in accordance with the invention may typically deliver a volume of liquid in a single spray actuation in the range of from 0.01 to 0.15 mL. A typical dosing regimen for a nasal spray product may be in the range of one spray into a single nostril (naris) to two sprays into each nostril (naris). Repeat dosing of the same nostril (naris) may also be undertaken. It is recognised that the dosing schedule, including a repeat dosing schedule, may be modified to obtain a desired pharmacokinetic profile. In one or more embodiments, repeat dosing may occur every 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In particular, repeat dosing may occur during waking hours. More preferably, repeat dosing in accordance with the invention may occur every 2, 4, 6 or 8 hours during waking hours.

The amount of rivastigmine administered per dose or the total volume of composition administered will depend on such factors as the nature and severity of the symptoms, the age, weight, and general health of the patient. In still other embodiments, repeat dosing may occur where a patient does not adequately respond to an initial dose, for example, by alleviation of one or more symptoms of dementia. In some embodiments, the intranasal pharmaceutical composition may deliver a unit dose of rivastigmine selected from about 0.05 to about 20 mg, about 0.10 to about 15 mg, about 0.15 to about 6 mg, about 0.2 to about 5 mg, about 0.3 to about 3 mg, about 0.6 to about 2.5 mg, about 1 to about 2 mg; about 1.25 to about 1.75 mg.

It is recognised that relative amounts of excipients, solvents, diluents, salts, thickening agents, sensory agents, buffers, and/or any additional ingredients in a pharmaceutical composition of the invention will vary, depending upon the identity, size, and/or condition of the subject treated.

In certain embodiments, unit dosage compositions are those containing a daily dose or unit, daily sub-dose, as herein above described, or an appropriate fraction thereof, of the active ingredient.

The intranasal formulations in accordance with the present invention may be contained in a kit. The kit may include, for example, rivastigmine and an additional agent, each packaged or formulated individually for intranasal administration, or packaged or formulated in combination. Thus, rivastigmine may be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising rivastigmine described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising rivastigmine and the second pharmaceutical composition contained in the kit may be optionally combined in the same pharmaceutical composition.

It may be desirable to provide written memory aid containing information and/or instructions for the physician, pharmacist or subject regarding when the medication is to be taken. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

In some aspects, rivastigmine could be provided in the form of a prodrug. The term "pro-drug" is used in its broadest sense and encompasses those derivatives that are converted in vivo to the compounds of the invention. Such derivatives would readily occur to those skilled in the art.

Furthermore, it is recognised that rivastigmine may be in crystalline form either as the free compound or as a solvate (e.g., hydrates) and it is intended that both forms are within the scope of the present invention. Methods of solvation are generally known within the art.

Those skilled in the art will be aware that the invention described herein is subject to variations and modifications other than those specifically described. It is to be understood that the invention described herein includes all such variations and modifications. The invention also includes all such steps, features, methods, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Certain embodiments of the invention will now be described with reference to the following examples which are intended for the purpose of illustration only and are not intended to limit the scope of the generality hereinbefore described.

EXAMPLES

Example 1: Diffusion Studies with Bovine Nasal Mucosa Over 6 Hours

Freshly excised, full-thickness, adult bovine nasal mucosa was placed into horizontal flow-through diffusion cells with a diffusional area of 1.0 $cm^2$ (Permegear, US). The mean thickness of the excised nasal mucosa used in the diffusion experiments for Formulations 1 to 4 was 760±40 μm (mean±SE, n=32). Following excision, the bovine nasal mucosa was floated in PBS at room temperature whilst awaiting placement in the diffusion cell. After placement in the diffusion cell, the surface of the nasal mucosa was gently blotted with a fine grade absorbable wipe to remove any excess PBS from the surface of the nasal mucosa. Diffusion experiments were performed over 12 to 24 h time periods. The receptor solution consisted of PBS, which was degassed under vacuum prior to the diffusion experiment. Eight diffusion cells were maintained at a flow rate of 1.3 ml/h by a microcassette peristaltic pump operating with 0.38 mm i.d. tubing (Watson Marlow 205S with O/G Marprene manifold tubing, UK) which ensured sink conditions were maintained. The cells were kept at 31° C. with a heater bar (Permegear, US) connected to a circulating water heater (Thermoline TU1, Australia). Samples were collected into 6.5 ml PP vials (Simport snaptwist, US) housed on an automated fraction collector (Teledyne Isco Retriever 500, US). Prior to analysis by RP-HPLC each vial was weighed on an analytical balance (Shimazdu AUW220D) connected to a personal computer and then the volume calculated in each vial from the density of the receptor solution which was about 1.0 $g/cm^3$. The nasal spray solutions were applied to the nasal mucosa of each diffusion cell with a 0.5 to 10 μL adjustable pipette (Mettler Toledo L-10XLS) at a dose volume of 5 μL per $cm^2$ unless otherwise stated.

The compositions of Formulations 1 to 4 are detailed in Table 1. Formulation 4, comprising an aqueous solution of rivasitgmine in citrate buffer at pH 3.65 was used as a control. The mean cumulative amount of rivastigmine (Q Riv) diffused after 6 hours across bovine nasal mucosa in vitro for each of Formulation 1 to 4 is detailed in Table 2.

TABLE 1

Composition of Formulations 1 to 4

|  | Formulation 1 | Formulation 2 | Formulation 3 | Control Formulation 4 |
| --- | --- | --- | --- | --- |
| Rivastigmine tartrate | 2.5% w/v | 2.5% w/v | 2.5% w/v | 2.5% w/v |
| Citric acid monohydrate | 0.05% w/v | 0.05% w/v | 0.05% w/v | 0.05% w/v |
| Sodium citrate | 0.25% w/v to a measured aqueous buffer pH of 3.65 | 0.25% w/v to a measured aqueous buffer pH of 3.65 | 0.25% w/v to a measured aqueous buffer pH of 3.65 | 0.25% w/v to a measured aqueous buffer pH of 3.65 |
| Carveol | 0.05% v/v | — | 0.05% v/v | — |
| Ethanol | 10% v/v | — | 10% v/v | — |
| Benzyl alcohol | 0.65% v/v | — | 0.65% v/v | — |
| USP Povidone | 1.0% w/v | 1.0% w/v | — | — |
| Purified water | to volume (100 mL) | to volume (100 mL) | to volume (100 mL) | to volume (100 mL) |

TABLE 2

Mean cumulative amount of rivastigmine (Q Riv) after 6 hours across bovine nasal mucosa in vitro

| Formulation No. | Q Riv 6 h (μg/$cm^2$ ± SE, n = 8) | % of Applied Dose |
| --- | --- | --- |
| 1 | 49 ± 3* | 63* |
| 2 | 42 ± 7 | 54 |
| 3 | 44 ± 5 | 56 |
| 4 (control) | 38 ± 4 | 49 |

*Statistically significantly different to 4(control), $p < 0.01$

TABLE 3

Mean cumulative amount of rivastigmine (Q Riv)
after 12, 18 and 24 hours across bovine nasal mucosa in vitro

| Formulation No. | Dose applied ($\mu$L/cm$^2$) | Time (h) to finite dose depletion | Q Riv ($\mu$g/cm$^2$ ± SE, n = 4) at depletion | % of Applied Dose | Dose Proportionality |
|---|---|---|---|---|---|
| 1 | 5 | 12 | 60 ± 9 | 77 | 1 |
| 1 | 10 | 18 | 142 ± 3 | 91 | 2.4 |
| 3 | 5 | 12 | 57 ± 7 | 73 | 1 |
| 3 | 10 | 16 | 121 ± 6 | 78 | 2.1 |
| 3 | 20 | 24 | 307 ± 9 | 98 | 5.4 |

Dose Proportionality, ratio of Q Riv divided by Q Riv for the lowest dose (i.e. 5 $\mu$L)

The mean cumulative amount of rivastigmine (Q Riv) that had diffused across the bovine nasal mucosa in vitro was measured after 6 hours was significantly greater (p<0.01) for Formulation 1 (round symbols) when compared with the control Formulation 4 (square symbols) over the same time period (Refer to FIG. 1, Tables 1 and 2). At 6 hours post-dose, the mean percentage of the applied dose penetrated was 63% and 49% for Formulation 1 and control Formulation 4, respectively (p<0.01). Formulation 1 provided a statistically significant 30% increase in the Q Riv after 6 hours (p<0.01).

Formulation 2, comprising an aqueous solution of rivastigmine in citrate buffer at pH 3.65 and thickening agent povidone was also compared with control Formulation 4 (Refer to Table 1 and 2). The addition of the thickening agent (Formulation 2) improved the diffusion of rivastigmine across nasal mucosa compared with the control formulation that contained drug and a citric acid pH modifier alone (Formulation 4).

Formulation 3, comprising an aqueous solution of rivastigmine in citrate buffer at pH 3.65, sensory agents (ethanol and carveol) and a preservative (benzyl alcohol) was also compared with control Formulation 4 (Refer to Table 1 and 2). The addition of the sensory agents, and preservative (Formulation 3) also improved the diffusion of rivastigmine across nasal mucosa compared with the control formulation that contained drug and a citric acid pH modifier alone (Formulation 4).

Example 2: Diffusion Studies with Bovine Nasal Mucosa Over 12 Hours

Figure 2:
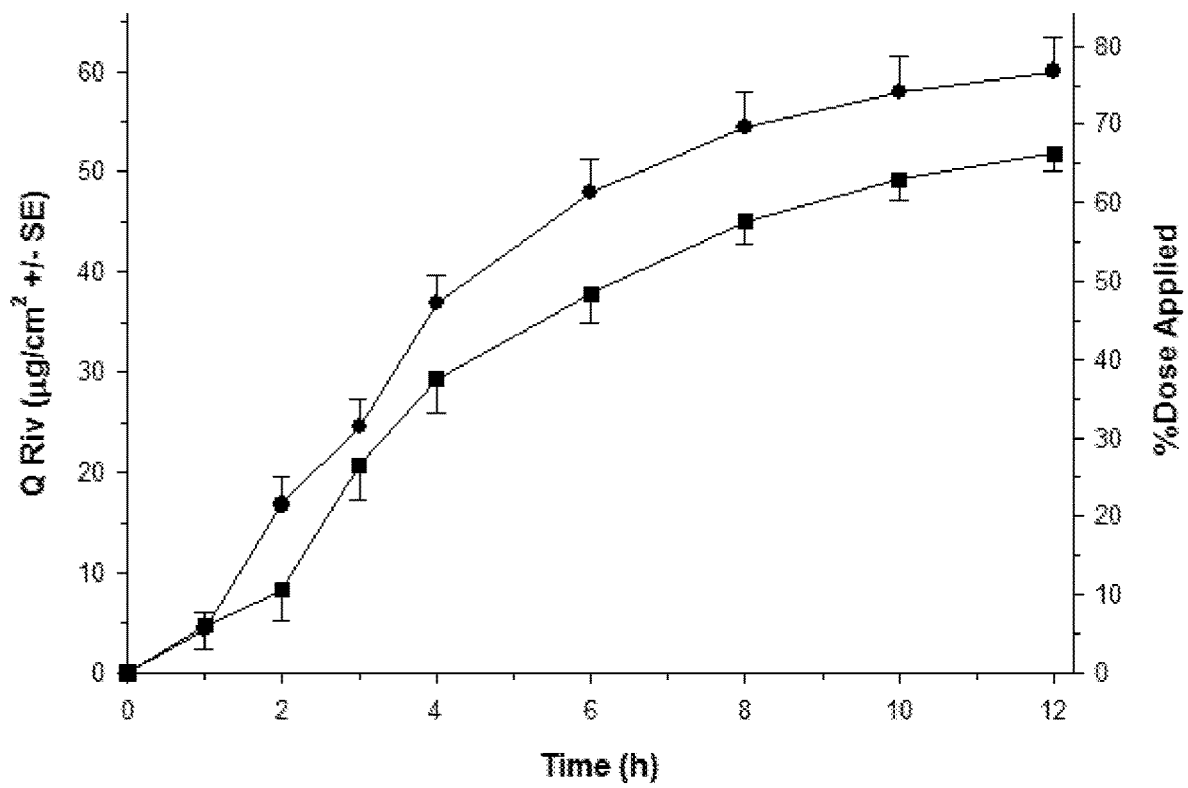

The mean cumulative amount of rivastigmine (Q Riv) that had diffused across the bovine nasal mucosa in vitro was also assessed after 12 hours for Formulation 1 (round symbols) when compared with the control Formulation 4 (square symbols; Refer to FIG. 2). Finite dose depletion of the diffusion profile was observed after 12 hours, with Q Riv at 12 hours for Formulation 1 (60±9 $\mu$g/cm$^2$, n=4) significantly greater (p<0.04) when compared with control Formulation 4 (52±6 $\mu$g/cm$^2$, n=8). At 12 hours post-dose, the formulation of Formulation 1 provided a statistically significant 16% increase in the Q Riv (p<0.04), the mean percentage of the applied dose penetrated was about 77% and 66% for Formulation 1 and control Formulation 4, respectively (p<0.04).

Figure 3:
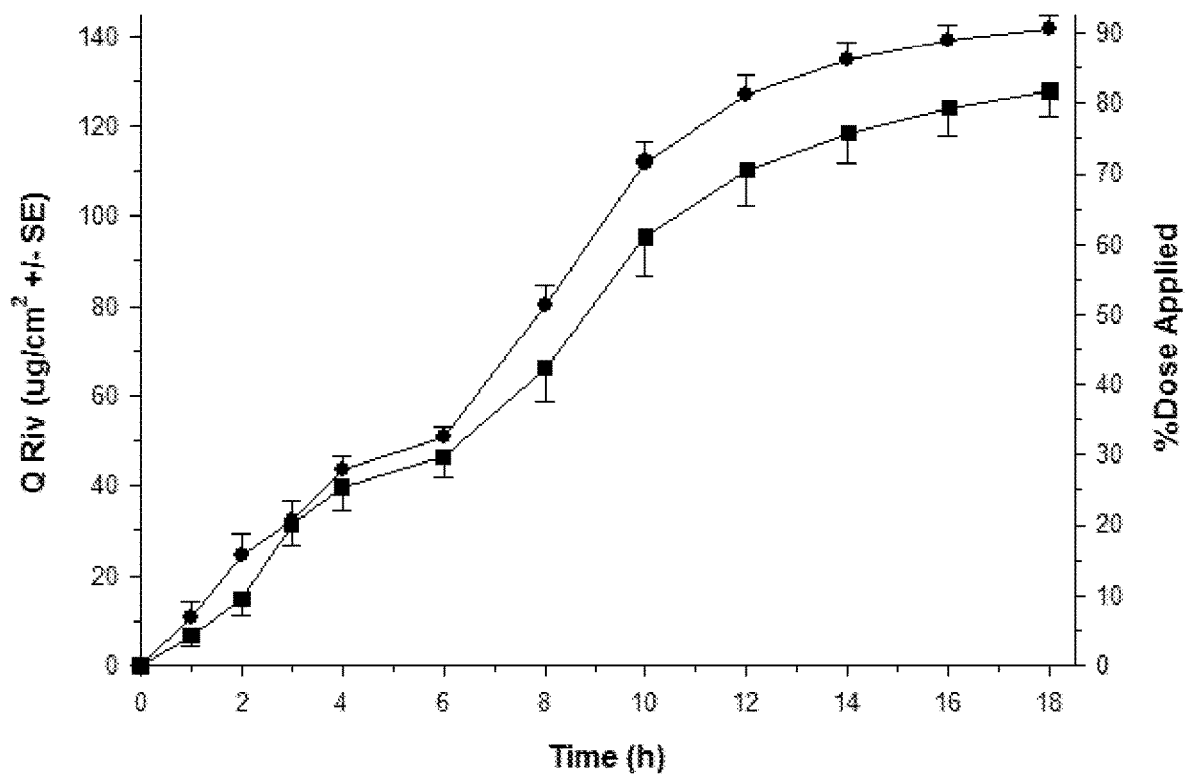

Example 3: Repeat Dosing Diffusion Studies with Bovine Nasal Mucosa at 0 and 6 Hours Repeat dosing of Formulation 1 at 0 and 6 hours (5 $\mu$L dose at each of t=0 and 6 hours) resulted in diffusion profiles that were zero-order in nature (Refer to FIG. 3). Individual diffusion profiles (n=4) each produced statistically significant linear regressions ($r^2$ range=0.962 to 0.987; F range=178 to 539; all p-values <0.001) when plotted from zero to 12 hours. The mean flux for Formulation 1 over 12 hours with repeat dosing was 11±1 $\mu$g/cm$^2$.h (mean±SE, n=4). FIG. 3 details the results of Q Riv for Formulation 1 (round symbols, n=4) and Formulation 2 (square symbols, n=4) with repeat dosing schedule. The mean percentage of the applied dose penetrated was about 91% and 82% respectively for Formulation 1 and Formulation 2, respectively (p<0.04).

Example 4: Diffusion Studies with Bovine Nasal Mucosa Over 24 Hours

Figure 4:
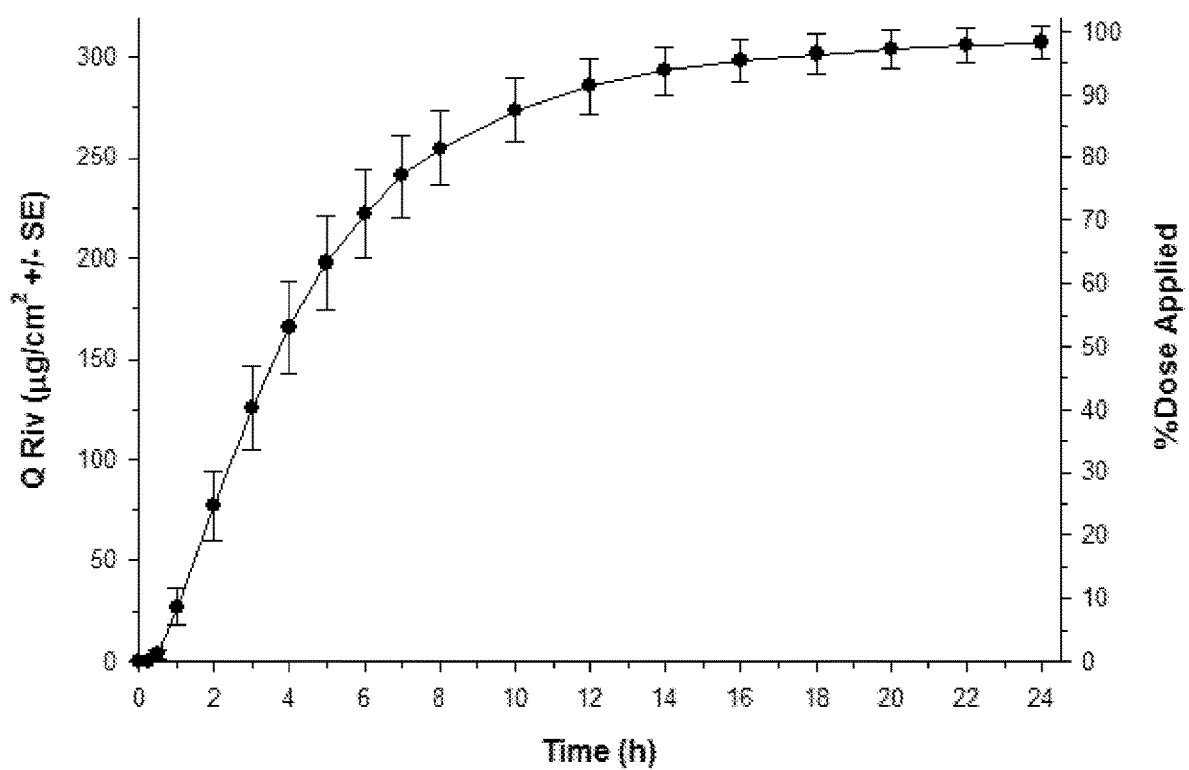
Figure 5:
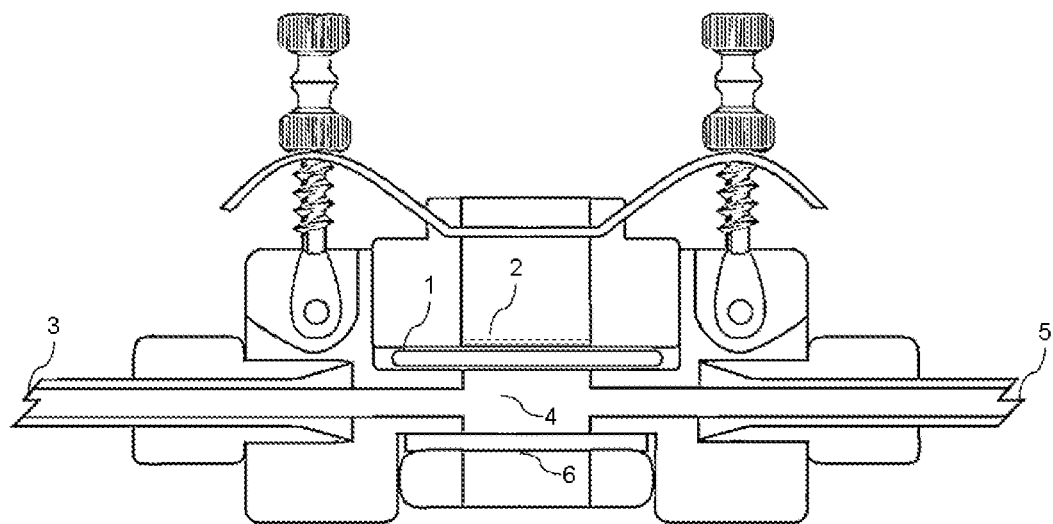
Figure 6:
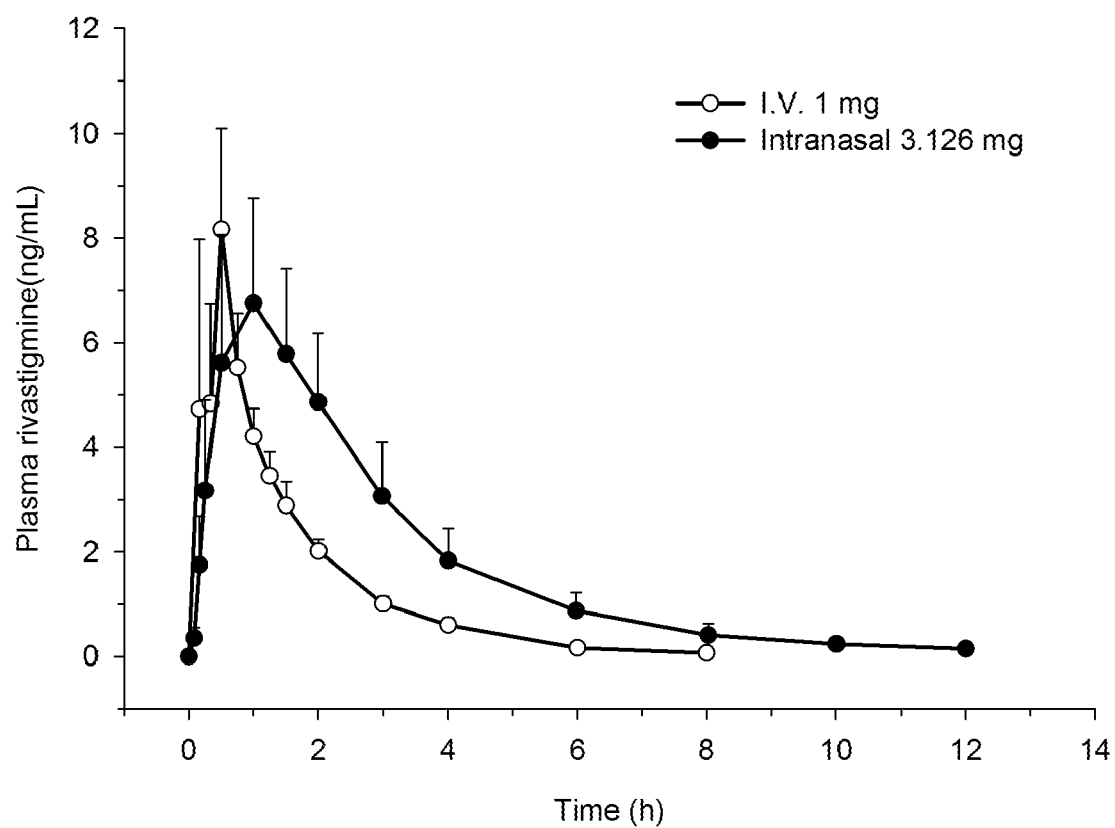
FIG. 6: Mean (±SD) plasma concentration-time profiles of rivastigmine after administration i) rivastigmine 1 mg as a constant intravenous infusion (○); or ii) 3.126 mg intranasal spray (●) in healthy elderly individuals (n=8).
Figure 7:
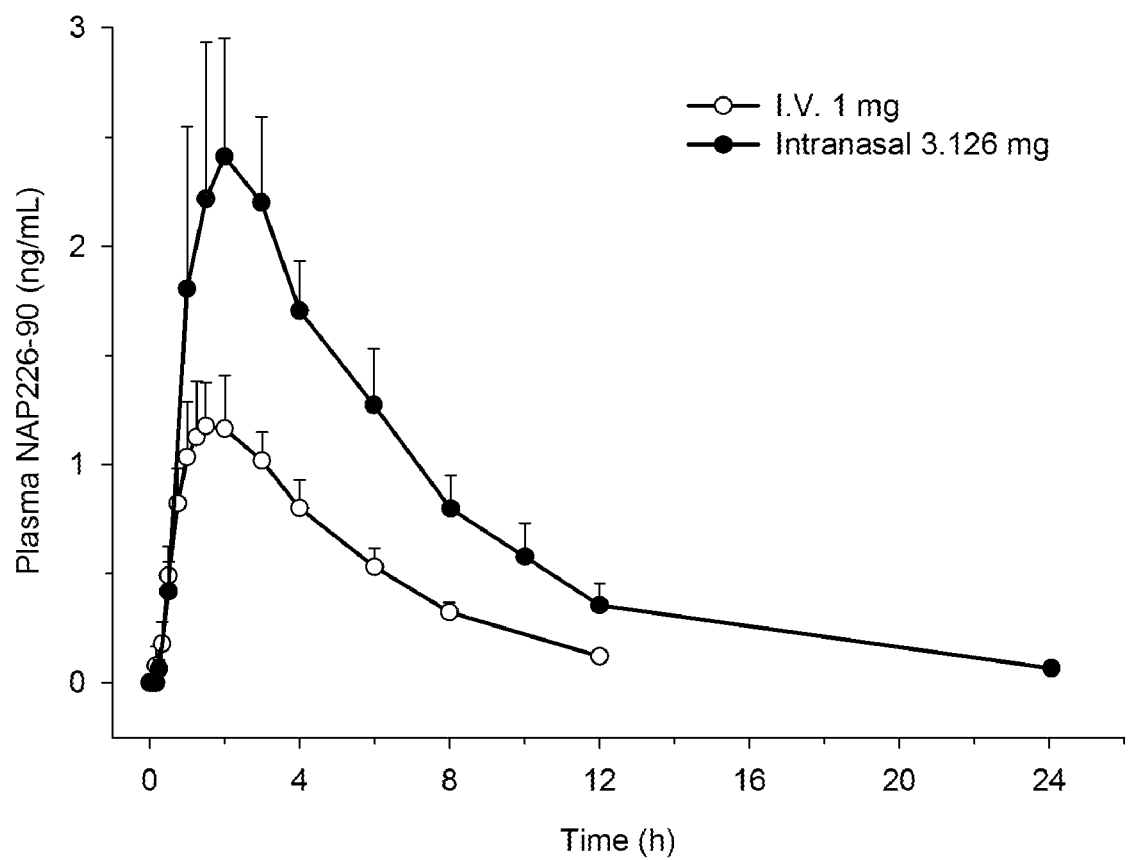
FIG. 7: Mean (±SD) plasma concentration-time profiles of NAP226-90 after administration of i) 1 mg rivastigmine 1 mg as a constant intravenous infusion (○); or ii) 3.126 mg intranasal spray (●) in healthy elderly individuals (n=8).

Following a single 20 $\mu$L/cm$^2$ dose of Formulation 3 to each diffusion cell (round symbols), the finite dose depletion of the diffusion profile was observed after 24 hours (Refer to FIG. 4). Q Riv at 6 hours, 12 hours and 24 hours for Formulation 3 was 222±22, 286±14 and 307±9 $\mu$g/cm$^2$ (n=4), respectively, or 71%, 91% and 98% of the applied dose, respectively. Freshly excised, bovine nasal mucosa is an accepted in vitro model to study drug permeability of the nasal epithelium (Schmidt et al. 2000) and can be used to estimate the systemic bioavailability in humans of compounds administered intranasally (Chemuturi et al. 2005). A drawing of the flow-through diffusion cell is shown in FIG. 5. The reliability of the dose proportionality of the in vitro bovine nasal mucosa model is shown by Table 3, where a doubling of the dose applied for each of Formulations 1 and 3 led to similar proportional increases in Q Riv. Without wishing to be bound by theory, the diffusion profiles obtained for the previous examples where consistent with Fick's second law of diffusion after a finite dose to the apical surface of a nasal membrane.

Example 5: Combination Intranasal Spray Comprising Rivastigmine and Dextromethorphan Detailed in Table 4 is an example of an intranasal formulation comprising rivastigmine tartrate and dextromethorphan hydrobromide within the same intranasal spray composition.

TABLE 4

| Component | % composition |
|---|---|
| Rivastigmine tartrate | 2.0% w/v |
| Dextromethorphan hydrobromide | 3.0% w/v |
| Citric acid monohydrate | 0.05% w/v |
| Sodium citrate | 0.25% w/v to a measured aqueous buffer pH of 3.65 |
| Carveol | 0.05% v/v |
| Ethanol | 10% v/v |
| Glycerol | 30% v/v |
| Benzyl alcohol | 0.65% v/v |
| Purified water | to volume (100 mL) |

Example 6: Intranasal Spray Comprising Dextromethorphan for Co-administration

Detailed in Table 5 is an example of an intranasal formulation comprising dextromethorphan hydrobromide which may be co-administered in combination with a rivastigmine intranasal spray composition, such as that described in Formulation 1.

TABLE 5

| Component | % composition |
| --- | --- |
| Dextromethorphan hydrobromide | 2.0% w/v |
| Citric acid monohydrate | 0.05% w/v |
| Sodium citrate | 0.25% w/v to a measured aqueous buffer pH of 3.65 |
| Carveol | 0.05% v/v |
| Ethanol | 10% v/v |
| Glycerol | 10% v/v |
| Benzyl alcohol | 0.65% v/v |
| Purified water | to volume (100 mL) |

Example 7: Combination Intranasal Spray Comprising Rivastigmine and Ifenprodil

Detailed in Table 6 is an example of an intranasal formulation comprising rivastigmine tartrate, dextromethorphan hydrobromide and ifenprodil hydrochloride within the same intranasal spray composition.

TABLE 6

| Component | % composition |
| --- | --- |
| Rivastigmine tartrate | 2.0% w/v |
| Dextromethorphan hydrobromide | 3.0% w/v |
| Ifenprodil hydrochloride | 0.25% w/v |
| Citric acid monohydrate | 0.05% w/v |
| Sodium citrate | 0.25% w/v to a measured aqueous buffer pH of 3.65 |
| Carveol | 0.05% v/v |
| Ethanol | 10% v/v |
| Glycerol | 30% v/v |
| Benzyl alcohol | 0.65% v/v |
| Purified water | to volume (100 mL) |

Example 8: Intranasal Spray Comprising Ifenprodil for Co-administration

Detailed in Table 7 is an example of an intranasal formulation comprising ifenprodil hydrochloride which may be co-administered in combination with a rivastigmine intranasal spray composition, such as that described in Formulation 1.

TABLE 7

| Component | % composition |
| --- | --- |
| Ifenprodil hydrochloride | 0.25% w/v |
| Citric acid monohydrate | 0.05% w/v |
| Sodium citrate | 0.25% w/v to a measured aqueous buffer pH of 3.65 |
| Carveol | 0.05% v/v |
| Ethanol | 10% v/v |
| Glycerol | 10% v/v |
| Benzyl alcohol | 0.65% v/v |
| Purified water | to volume (100 mL) |

Example 9: Combination Intranasal Spray Comprising Rivastigmine and Encenicline

Detailed in Table 8 is an example of an intranasal formulation comprising rivastigmine tartrate and encenicline hydrochloride within the same intranasal spray composition.

TABLE 8

| Component | % composition |
| --- | --- |
| Rivastigmine tartrate | 2.0% w/v |
| Encenicline hydrochloride | 1.5% w/v |
| Citric acid monohydrate | 0.05% w/v |
| Sodium citrate | 0.25% w/v to a measured aqueous buffer pH of 3.65 |
| Carveol | 0.05% v/v |
| Ethanol | 10% v/v |
| Glycerol | 10% v/v |
| Benzyl alcohol | 0.65% v/v |
| Purified water | to volume (100 mL) |

Example 10: Intranasal Spray Comprising Encenicline for Co-administration

Detailed in Table 9 is an example of an intranasal formulation comprising encenicline hydrochloride which may be co-administered in combination with a rivastigmine intranasal spray composition, such as that described in Formulation 1.

TABLE 9

| Component | % composition |
| --- | --- |
| Encenicline hydrochloride | 2.0% w/v |
| Citric acid monohydrate | 0.05% w/v |
| Sodium citrate | 0.25% w/v to a measured aqueous buffer pH of 3.65 |
| Carveol | 0.05% v/v |
| Ethanol | 10% v/v |
| Benzyl alcohol | 0.65% v/v |
| Purified water | to volume (100 mL) |

Example 11: Intranasal Spray Comprising Rivastigmine

Detailed in Table 10 is an example of an intranasal formulation comprising rivastigmine tartrate at a higher concentration.

TABLE 10

| Component | % composition |
| --- | --- |
| Rivastigmine tartrate | 5.0% w/v |
| Citric acid monohydrate | 0.055% w/v |
| Carveol | 0.05% v/v |
| Ethanol | 10% v/v |
| Benzyl alcohol | 0.65% v/v |
| Polyvinyl pyrrolidone | 1.0% w/v |
| Purified water | to volume (100 mL) |

Example 12: Absolute Bioavailability and Safety Study of Rivastigmine Intranasal Spray in Healthy Elderly Indviduals Methods The safety and absolute bioavailability of an intranasal formulation in accordance with the invention was examined by clinical trial. The study was approved by The Alfred Hospital Human Research and Ethics Committee, Melbourne, Australia and prospectively registered with the Australia and New Zealand Clinical Trial Registry (ANZCTR), Trial ID ACTRN12614001313628. The study was conducted at the clinical trial unit of Nucleus Network Limited (Melbourne, Australia) and independently monitored by Commercial Eyes Pty Ltd (Melbourne, Australia) in accordance with Good Clinical Practice (GCP) and the principles of the Declaration of Helsinki.

Design

The study was of open label, sequential, crossover design in eight healthy elderly female and male Caucasian volunteers who all gave written informed consent to participate in the study. On day 1, intravenous rivastigmine (1 mg) was administered to each participant as a constant intravenous infusion over 30 minutes, followed by a washout period of two days (days 2 and 3). On day 4, a rivastigmine intranasal spray (3.126 mg) was administered to each participant as a single dose comprising one spray in each nostril.

Key inclusion criteria for participation in the study included:
Healthy Caucasian males and females between 55 and 85 years (inclusive) of age;
No known history of clinically significant neurological, renal, cardiovascular, respiratory (asthma), endocrinological, gastrointestinal, haematopoietic disease, neoplasm or any other clinically significant medical disorder, which in the Principal Investigator's judgment contraindicate administration of the study interventions;
BMI 18-32 (inclusive) calculated as Weight (kg)/Height (m$^2$)
Non-smoking (by declaration) for a period of at least 6 months.

Key exclusion criteria included:
Known hypersensitivity to the drug, components (benzyl alcohol, benzoates) or other carbamates;
Current symptomatic allergic rhinitis;
History of or currently active asthma or chronic obstructive pulmonary disease, excluding childhood asthma;
History of or currently active cardiac arrhythmias such as bradycardia and sick sinus syndrome;
History of urinary tract obstruction;
History of or currently active GI diseases such as peptic ulcer, GERD, bleeding or history of any GI surgery other than appendectomy or herniotomy, or with any gastrointestinal disorder likely to influence drug absorption, or with any history of anorexia, frequent nausea or emesis, regardless of etiology;
Use of any beta-blocker class prescription drug, cholinomimetic and anticholinergic drugs, including atropine, tricyclic antidepressants and anti-histamines.

Clinical

Detailed in Table 11 is the intranasal spray formulation in accordance with the invention administered during the clinical trial:

TABLE 11

| Component | % composition |
|---|---|
| Rivastigmine tartrate | 2.5% w/v |
| Citric acid monohydrate | 0.055% w/v |
| Carveol | 0.05% v/v |
| Ethanol | 10% v/v |
| Benzyl alcohol | 0.65% v/v |
| Polyvinyl pyrrolidone | 1.0% w/v |
| Distilled water | to volume |

The abovementioned formulation was filled into 20 ml high-density polyethylene bottles and sealed with 100 μL VP7 metered-dose pump valves with nasal spray actuators and caps (Aptar, Le Vaudreuil, F R) and had a final pH of 3.6. One 100 μL spray (2.5 mg rivastigmine tartrate equivalent to 1.563 mg rivastigmine free base) was administered into each nostril by study staff for a total single-dose of 3.126 mg rivastigmine. The shot weight delivered to each participant was determined by weighing the intranasal spray device before and after each dosing each participant. The amount of rivastigmine delivered to each participant was determined from the shot weight, density and concentration of the intranasal spray formulation.

Detailed in Table 12 is the solution of rivastigmine administered intravenously as a control in the clinical trial:

TABLE 12

| Component | % composition |
|---|---|
| Rivastigmine tartrate | 0.032% w/v |
| Citric acid monohydrate | 0.022% w/v |
| Distilled water | To provide 1 mg rivastigmine per 5 mL |

The abovementioned solution was sterilised by filtration then aseptically filled into sealed type 1 glass vials. For intravenous (i.v.) administration, 6 ml of the i.v. solution was diluted to 30 ml with 5% glucose for injection and 25 ml (1 mg rivastigmine) was administered as a constant infusion over 30 min using a volumetrically controlled syringe driver. The infusion line was primed prior to start of the infusion.

Blood samples were taken from the non-dominant arm of each participant i) for the i.v. treatment at time point 0 (pre-administration), 10 min, 20 min, 30 min, 45 min, 60 min, 75 min, 90 min; 2 h, 3 h, 4 h, 6 h, 8 h, 12 h and 24 h post-administration, and ii) for the intranasal treatment at time point 0 (pre-administration), 5 min, 10 min, 15 min, 30 min, 60 min, 90 min; 2 h, 3 h, 4 h, 6 h, 8 h, 10 h, 12 h and 24 h post-administration.

Blood was collected into $K_2$ EDTA tubes, and immediately transferred to a pre-chilled polypropylene centrifuge tube, containing sodium fluoride (110 μL of a 1M sodium fluoride solution per 1 mL blood) to inhibit any ex vivo enzymatic breakdown of the parent compound and its metabolite. The whole blood sample was centrifuged at 3000 rpm (about 1900 g), 3° to 5° C., for 10 min, and the harvested plasma transferred to a polypropylene cryo-tube and stored frozen at −20° C. pending analysis.

Visual nasal mucosal examination occurred at screening, check-in, on day 4 (pre-nasal-dose) and day 5 (24 hours post-nasal-dose). Adverse events and vital signs (blood pressure, heart rate, respiratory rate, oral body temperature) were monitored from Day 1 until Day 5 (24 hours post-nasal-dose) and at follow-up visit (Day 9+/−1). For the elicitation of potential adverse events relating to nasal mucosal irritation a series of relevant tolerability questions (stinging, itching, burning sensations in nose or throat, rhinalgia and lacrimation) were sought from the participants with a 5-point Likert-scale for the responses using a perceived nasal irritation questionnaire. This assessment was completed at 20 and 75 minutes following the intranasally administered dose. Participants rated perceived nasal irrigation across the following criteria: 1. Stinging in the nose; 2. Itching in the nose; 3. Burning the nose; 4. Causing a runny nose; 5. Stinging in the throat; 6. Itching in the throat; 7. Burning in the throat; and 8. Causing watery eyes. Participants graded each criterion according to the following scale: i) Not at All; ii) Mildly; iii) Moderately; iv) Somewhat markedly; or v) Very Markedly.

A healthy screen pre- and post-study was completed for all participants. The healthy screen included:

Physical examination, including vital signs (blood pressure, heart rate, respiratory rate and temperature) and ECG;

Urinalysis for general health (urine pH, blood, protein, ketones, leukocyte elastase, nitrates, glucose, Specific gravity, urobilinogen and bilirubin) and any drugs of addiction*. Blood collected for clinical laboratory analysis (serum chemistry and haematology) and analysis for HIV*, hepatitis B*, and hepatitis C* analysis. Normal ranges for clinical laboratory parameters will be as per the local laboratory definitions (*pre-study).

Bioanalytical Assay

Analysis of rivastigmine and its primary metabolite, 3-[(1S)-1-(dimethylamino)ethyl]phenol (hereafter "NAP 226-90") was performed by the bioanalytical division of Anapharm Europe (Barcelona, SP). Rivastigmine, NAP 226-90 and internal standards were extracted from an aliquot of human EDTA plasma using a liquid-liquid extraction procedure with ethyl acetate and then injected into a liquid chromatograph equipped with a tandem mass spectrometry detector (LC/MS/MS). Separations were performed on a reversed-phase column (Zorbax SB-C18, 4.6×50 mm, 5 µm, from Agilent Technologies). Mobile phase A was ammonium acetate 10 mM at pH 5 prepared in water and mobile phase B was ammonium acetate 10 mM prepared in methanol. The chromatographic separation was gradiently performed at room temperature at a flow-rate from 1.00 to 1.10 mL/min. The calibration range used for this assay was from 0.05 to 20 ng/mL for rivastigmine and from 0.05 to 10 ng/mL for NAP 226-90. The assay passed linearity for rivastigmine (r >0.997) and NAP226-90 (r >0.997) over each of the calibration ranges tested. Accuracy and precision at the LLOQ (0.05 ng/mL) for rivastigmine were 5.65% and ±2.72%, respectively. Accuracy and precision at the LLOQ (0.05 ng/mL) for NAP226-90 were 5.79% and ±2.72%, respectively. Precision and accuracy for all the remaining concentrations in each calibration range were also within their acceptance limits.

Non-compartmental Pharmacokinetic Analysis

Area under the curve (AUC) was taken from the blood plasma concentration-time profile. AUC to the last measured concentration (AUC0-1), AUC over a time interval (AUC0-6 h) and AUC zero to infinity (AUC0-∞) were calculated by the linear trapezoidal rule using Sigmaplot (version 12.5; Systat Software, Inc. San Jose, USA). The maximum plasma concentration ($C_{max}$) and time to maximum plasma concentration ($T_{max}$) were determined by visual inspection of the data. Absolute bioavailability (F) was calculated as AUC0-∞ nasal/nasal dose divided by AUC0-∞ i.v./i.v. dose. Terminal elimination half-life ($t_{1/2}$) was defined as 0.693/λ, where λ is the terminal elimination rate constant (calculated from the slope of the regression line of the terminal phase of the natural logarithm of concentration versus time). Average plasma concentration ($C_{avg}$) was calculated from the AUC over a time interval ($AUC_{0-6h}$) divided by the prospective dosage interval (6 h). Fluctuation index (FI) equalled ($C_{max}$-$C_{min}$) divided by $C_{avg0-1}$. $C_{avg0-1}$ was calculated as AUC0-1 divided by the time for the last measured concentration. Metabolite (NAP226-90) to parent ratio was calculated by dividing AUC0-∞ of NAP-226-90 divided by AUC0-∞ of rivastigmine. Systemic clearance (CL=IV dose/AUC0-∞ i.v.) and volume of distribution (Vz=i.v. dose/λ●AUC0-∞ i.v.) were calculated for the i.v. dose.

Statistical Analysis

To meet the primary hypothesis that absolute bioavailability (F) is >0, a one-sample Student's t-test using a mean (SD) F=0.5 (0.25) and n=4, provides a Power of 0.908 when performed as a one-tailed test with alpha=0.050 using Sigmaplot analysis (version 12.5; Systat Software, Inc. San Jose, Calif., USA). This conservative (mean and variation) estimate for F, was based on the existing in vitro diffusion data for the rivastigmine intranasal spray formulation and consideration of the extent and variability of nasal absorption in humans for other drugs with comparable physicochemical properties. Statistical significance was determined by a one-sample Student's t-test, or a non-parametric one-sample Wilcoxon signed-rank test, if for example the raw F data are not normally distributed. Pharmacokinetic parameters were tabulated as mean values with their standard deviation and percentage coefficient of variation (CV %).

Table 13 details the non-compartmental pharmacokinetic parameters of rivastigmine after administration of rivastigmine 1 mg as a constant intravenous infusion or 3.126 mg intranasal spray in healthy elderly individuals (n=8).

TABLE 13

| Rivastigmine Parameter | Intranasal Spray | | | Intravenous Solution | | |
|---|---|---|---|---|---|---|
| | Mean ± SD | CV % | Range | Mean ± SD | CV % | Range |
| $C_{max}$ (ng/mL) | 6.9 ± 2.0 | 29 | 4.6-9.8 | 8.5 ± 1.8 | 22 | 5.8-11.2 |
| $T_{max}$ (h) | 1.1 ± 0.5 | 46 | 0.5-2.0 | 0.5[a] | 0.5-0.5[b] | 0.2-0.5 |
| $AUC_{0-1}$ (ng · h/mL) | 21.9 ± 6.3 | 29 | 13.2-31.9 | 11.5 ± 1.4 | 12 | 8.7-13.7 |
| $AUC_{0-\infty}$ (ng · h/mL) | 22.6 ± 6.2 | 28 | 13.5-32.7 | 11.6 ± 1.4 | 12 | 8.9-13.9 |
| $t_{1/2}$ (h) | 2.6[a] | 2.2-5.0[b] | 2.0-13.3 | 1.3 ± 0.1 | 8 | 1.2-1.4 |
| F % | 62 ± 15 | 25 | 45-85 | Ref | | |
| $AUC_{0-6h}$ (ng · h/mL) | 19.4 ± 5.7 | 30 | 11.8-27.5 | | | |
| $C_{avg0-6h}$ (ng/mL) | 3.2 ± 1.0 | 32 | 2.0-4.6 | | | |
| FI | 3.7[a] | 3.1-4.5[b] | 2.8-10.0 | | | |
| CL (L/h) | | | | 86.6 ± 11.9 | 14 | 71.8-112.2 |
| Vz (L) | | | | 163.8 ± 25.6 | 16 | 131.5-210.8 |

[a]Median;
[b]95% C.I.;
Ref, Reference

Table 14 details the non-compartmental pharmacokinetic parameters of NAP226-90 after administration of rivastigmine 1 mg as a constant intravenous infusion or 3.126 mg intranasal spray in healthy elderly individuals (n=8) with the invention are indicative that nasal absorption is the dominant absorption pathway, and further suggests oral absorption due to nasal mucociliary clearance (Merkus et al. 1998) is limited.

TABLE 14

| NAP226-90 | Intranasal Spray | | | Intravenous Solution | | |
|---|---|---|---|---|---|---|
| Parameter | Mean ± SD | CV % | Range | Mean ± SD | CV % | Range |
| $C_{max}$ (ng/mL) | 2.5 ± 0.6 | 24 | 2.0-3.4 | 1.2 ± 0.2 | 17 | 1.0-1.6 |
| $T_{max}$ (h) | 2.1 ± 0.8 | 39 | 1.0-3.0 | 1.9 ± 0.6 | 32 | 1.3-3.0 |
| $AUC_{0-t}$ (ng · h/mL) | 16.1 ± 2.2 | 14 | 12.8-19.1 | 6.7 ± 0.9 | 14 | 5.8-8.1 |
| $AUC_{0-\infty}$ (ng · h/mL) | 16.9 ± 2.3 | 14 | 13.8-20.5 | 7.2 ± 1.0 | 14 | 6.1-8.8 |
| $t_{1/2}$ (h) | 3.9 ± 0.8 | 21 | 2.9-4.6 | 2.8 ± 0.3 | 11 | 2.5-3.2 |
| FI | 2.8 ± 0.6 | 21 | 2.0-3.6 | | | |
| NAP226-90 $AUC_{0-\infty}$ to Rivastigmine $AUC_{0-\infty}$ ratio | 0.78 ± 0.19 | 25 | 0.66-1.15 | 0.63 ± 0.11 | 18 | 0.46-0.79 |

The study met the primary endpoint because the mean absolute bioavailability (F) for rivastigmine intranasal spray was 62%, representing a statistically significant result (p<0.001) when tested against F >0. In this initial trial, the observed variability in nasal absorption and metered-dosing was about 16%, while the non-dose adjusted percentage coefficient of variation (CV %) for rivastigmine AUC0-∞ was 28% and 12% for the intranasal and IV doses, respectively. The intranasal spray in accordance with the invention exhibited significantly (p<0.001) higher absolute bioavailability (62±15%, n=8) compared to the oral capsule (36±13%, n=12) and transdermal patch (45±10%, n=30; measured from post-usage drug residuals) in healthy elderly volunteers (Polinsky 1998, US FDA NDA No. 20-823, Lefèvre et al. 2008a, US FDA NDA No. 22-083). The mean clearance (86.6 L/h) and volume of distribution (163.8 L) for the 1 mg i.v. dose in this study was within the ranges previously observed for Alzheimer's disease patients administered a 2 mg i.v. dose (CL 21.6-82.8 L/h and Vz 53.2-227 L) (Hossain et al. 2002).

The initial clinical trial confirmed that rivastigmine, when administered as an intranasal formulation in accordance with the invention, was rapidly absorbed across the nasal mucosa with a mean (±SD)$T_{max}$ of 1.1±0.5 h and a mean $C_{max}$ of 6.9±2.0 ng/mL. The extent of absorption of rivastigmine was clinically significant. Furthermore, the results from this trial indicate that the $C_{avg}$ over the first 6 h after administration of the intranasal formulation could reasonably be expected to have an appreciable inhibitory effect on central acetylcholinesterase levels in Alzheimer's disease patients (Cutler et al. 1998 and Gobburu et al. 2001).

The NAP226-90 to rivastigmine ratio for AUC0-∞ were 0.78±0.19 and 0.63±0.11, for the intranasal and i.v. treatments, respectively. This ratio is comparable to that previously measured for the transdermal patch (0.67), and is advantageously 4-fold lower than the oral capsule (3.49) (Lefèvre et al. 2008a). It is generally recognised that a high degree of first-pass metabolism in the liver and gut after oral administration of rivastigmine results in much higher peripheral exposure to the metabolite (NAP226-90) (Polinsky 1998). The high F and low NAP226-90: rivastigmine AUC ratio observed for the intranasal sprays in accordance Initial examination of single dose safety for rivastigmine intranasal sprays in accordance with the present invention indicate the solutions are safe to administer with limited or no side effects. Only two minor adverse events relating to rivastigmine intranasal spray were recorded, i) one individual had mild nasal congestion and ii) a second individual had a mild, red, itchy stomach rash. Both participants recovered within 12 hours without treatment. Any minor nasal irritation or throat irritation was perceived by participants as mild and transient, and had resolved at 20 minutes post-nasal-dose.

Advantageously, no nausea, vomiting and diarrhoea (NVD) was observed with intranasal administration of rivastigmine despite the systemic dose being equivalent to a single 5.6 mg oral dose (i.e. 2.0 mg/Foral 0.355). Adverse gastrointestinal events (nausea, vomiting, diarrhea, weight loss and anorexia) have been significantly correlated with exposure to the metabolite NAP226-90 (both $C_{max}$ and AUC) resulting from first-pass metabolism in the liver and gut after oral administration of rivastigmine. No such correlation is associated with exposure to rivastigmine itself in the absence of the metabolite (US FDA NDA No. 20-823, Spencer and Noble 1998). The observed reduction or elimination of adverse gastrointestinal side effects with intranasal administration of rivastigmine represents a significant advantage. It has been suggested low rivastigmine fluctuation index (FI) may reduce oral-related adverse gastrointestinal events by administration of rivastigmine via a transdermal patch (median FI, 0.7; Kurz et al. 2009; Lefèvre et al. 2008b). However, advantageously, no NVD adverse events were observed even though the median rivastigmine FI (3.7) after intranasal administration was similar to the median rivastigmine FI (4.2) after oral administration (Lefèvre et al. 2008b).

The metered-dose intranasal spray has inherent capability to provide improved individual dosage adjustment within, below and above an effective dosing range. This may be beneficial because the intrinsic clearance (CL) of rivastigmine varies up to 4-fold in Alzheimer's disease patients (Hossain et al. 2002). For example, variability in intrinsic clearance was observed in patients in the present study who exhibited a mean i.v. intrinsic clearance 38% higher than that commonly observed in Alzheimer's disease (AD) patients (Hossain et al. 2002), consistent with other observations (29%, US FDA NDA No. 20-823). In such circumstances, it is recognised that a metered-dose intranasal spray in accordance with the invention may advantageously provide improved individual dosage adjustment.

In the present clinical trial, an intranasal dose of two sprays (i.e. one 100 μL spray in each nostril) delivered a mean systemic rivastigmine dose of 2 mg. For rivastigmine a few hours of the correct pharmacokinetic exposure in an Alzheimer's disease patient can provide up to half a day of central AChE inhibition (Cutler et al. 1998 and Gobburu et al. 2001). As indicated in the present clinical trial, the use of a rivastigmine intranasal spray in accordance with the invention at a dose, for example, of 2 to 3 sprays twice-daily may deliver comparable rivastigmine exposure and efficacy as a 6 to 9.7 mg/d oral dose and a 10 cm² transdermal patch, respectively (e.g. 9.7 mg oral×$F_{oral}$ 0.602=5.84 mg≈5.84/2.0=2.92 sprays twice-daily) (Winblad et al. 2007, Hossain et al. 2002). Furthermore, an estimated dose of a intranasal spray in accordance with the invention comparable to the 10 cm² transdermal patch, may reduce the cholinergic burden exposure by 55% based on the geometric mean AUC exposures for rivastigmine and NAP226-90 (i.e. ((21.9×3/99.5)−1)%+((16.7×3/63.8)−1)%=−55%) (Lefèvre et al. 2008a). It is considered that removing undesirable cholinergic burden by using rapid-onset dosing with an intranasal spray in accordance with the present invention during waking hours has the potential to allow a patient to move further up the dose-response curve (Imbimbo 2001).

As indicated from abovementioned clinical trial results, a rivastigmine intranasal spray in accordance with the invention may advantageously provide improved absolute bioavailability, rapid onset of action, low NAP226-90 to rivastigmine exposure ratio, a favourable safety and tolerability profile and/or flexible dosage adjustment.

Example 13: Viscosity of Intranasal Spray Composition

The viscosity of the rivastigmine intranasal spray composition described in Example 12 was determined using a falling-ball-type viscometer with glass ball (Gilmont, Thermo Scientific, USA). To calculate viscosity, the Viscometer constant (K)=Viscosity in centipoise (cP) divided by [(Density of the glass ball; 2.53 g/cm³−Density of the liquid being tested; 0.9991 g/cm³ water or 0.9932 g/cm³ Ex.11 composition) is multiplied by Time of descent in minutes]. The viscosity experiment was conducted at ambient temperature (15° C.) and ultrapure water was used to verify the viscometer constant (K) using the known viscosity of water of 1.1375 cP at 15° C. (IAPWS 2008). Based on two concordant measurements of Time of descent, the mean viscosity of the rivastigmine intranasal composition of Example 11 was 1.5 cP at 15° C. (or an estimated 1.2 cP at 25° C.).

REFERENCES

Araujo J A, Greig N H, Ingram D K, Sandin J, de Rivera C, Milgram N W. Cholinesterase inhibitors improve both memory and complex learning in aged beagle dogs. *J Alzheimers Dis.* 2011; 26(1): 143-55.
Birks J, Grimley Evans J, Iakovidou V, Tsolaki M, Holt F E. Rivastigmine for Alzheimer's disease. Cochrane Database Syst Rev. 2009 Apr. 15; (2):CD001191.
Birks J S, Grimley Evans J. Rivastigmine for Alzheimer's disease. Cochrane Database Syst Rev 2015; 4:CD001191.
Chemuturi N V, Hayden P, Klausner M, Donovan M D. Comparison of human tracheal/bronchial epithelial cell culture and bovine nasal respiratory explants for nasal drug transport studies. *J Pharm Sci.* 2005 September; 94(9):1976-85.
Cutler N R, Polinsky R J, Sramek J J, Enz A, Jhee S S, Mancione L, Hourani J, Zolnouni P. Dose-dependent CSF acetylcholinesterase inhibition by SDZ ENA 713 in Alzheimer's disease. *Acta Neurol Scand* 1998; 97:244-50.
Davies B, Morris T. Physiological parameters in laboratory animals and humans. *Pharm Res.* 1993 July; 10(7):1093-5.
Falck E, Begrow F, Verspohl E, Wunsch B. Metabolism studies of ifenprodil, a potent GluN2B receptor antagonist. *J Pharm Biomed Anal.* 2014 January; 88:96-105.
Feldman H H, Lane R; Study 304 Group. Rivastigmine: a placebo controlled trial of twice daily and three times daily regimens in patients with Alzheimer's disease. *J Neurol Neurosurg Psychiatry.* 2007 October; 78(10):1056-63.
Gobburu J V, Tammara V, Lesko L, Jhee S S, Sramek J J, Cutler N R, Yuan R. Pharmacokinetic-pharmacodynamic modeling of rivastigmine, a cholinesterase inhibitor, in patients with Alzheimer's disease. *J Clin Pharmacol.* 2001 October; 41(10):1082-90.
González-Martínez A, Rosado B, Pesini P, García-Belenguer S, Palacio J, Villegas A, Suarez M L, Santamarina G, Sarasa M. Effect of age and severity of cognitive dysfunction on two simple tasks in pet dogs. *Vet J.* 2013 October; 198(1): 176-81.
Grossberg G T, Sadowsky C, Olin J T. Rivastigmine transdermal system for the treatment of mild to moderate Alzheimer's disease. *Int J Clin Pract.* 2010 April; 64(5): 651-60.
Hossain M, Jhee S S, Shiovitz T, McDonald C, Sedek G, Pommier F, Cutler N R. Estimation of the absolute bioavailability of rivastigmine in patients with mild to moderate dementia of the Alzheimer's type. *Clin Pharmacokinet.* 2002; 41(3):225-34.
Imbimbo B P. Pharmacodynamic-tolerability relationships of cholinesterase inhibitors for Alzheimer's disease. *CNS Drugs* 2001; 15:375-90.
Klein M, Musacchio J M. High-affinity dextromethorphan and (+)-3-(-3-hydroxyphenyl)-N-(1-propyl)piperidine binding sites in rat brain. Allosteric effects of ropizine. *J Pharmacol Exp Ther.* 1992 March; 260(3):990-9.
Kukanich B, Papich M G. Plasma profile and pharmacokinetics of dextromethorphan after intravenous and oral administration in healthy dogs. *J Vet Pharmacol Ther.* 2004 October; 27(5):337-41.
Kurz A, Farlow M, Lefèvre G. Pharmacokinetics of a novel transdermal rivastigmine patch for the treatment of Alzheimer's disease: a review. *Int J Clin Pract.* 2009 May; 63(5): 799-805.
Lamer A J. Transdermal rivastigmine for Alzheimer's disease: skin deep or scratching the surface? *Int J Clin Pract.* 2010 April; 64(5):534-6.
Lefèvre G, Pommier F, Sedek G, Allison M, Huang H L, Kiese B, Ho Y Y, Appel-Dingemanse S. Pharmacokinetics and bioavailability of the novel rivastigmine transdermal patch versus rivastigmine oral solution in healthy elderly subjects. *J Clin Pharmacol* 2008a; 48:246-52.
Lefèvre G, Sedek G, Jhee S S, Leibowitz M T, Huang H L, Enz A, Maton S, Ereshefsky L, Pommier F, Schmidli H, Appel-Dingemanse S. Pharmacokinetics and pharmacodynamics of the novel daily rivastigmine transdermal patch compared with twice-daily capsules in Alzheimer's disease patients. *Clin Pharmacol Ther* 2008b; 83:106-14.

Maidment I, Fox C, Boustani M. Cholinesterase inhibitors for Parkinson's disease dementia. Cochrane Database Syst Rev 2006; 1:CD004747.

Merkus F W, Verhoef J C, Schipper N G, Marttin E. Nasal mucociliary clearance as a factor in nasal drug delivery. *Adv Drug Deliv Rev* 1998 29:13-38.

Miller S C. Dextromethorphan psychosis, dependence and physical withdrawal. *Addict Biol.* 2005 December; 10(4):325-7.

Miller S C. Dextromethorphan to dextrorphan: a pathway towards abuse liability. *Hum Psychopharmacol.* 2011 January; 26(1):89-90.

Moghadamnia A A, Rostami-Hodjegan A, Abdul-Manap R, Wright C E, Morice A H, Tucker G T. Physiologically based modelling of inhibition of metabolism and assessment of the relative potency of drug and metabolite: dextromethorphan vs. dextrorphan using quinidine inhibition. *Br J Clin Pharmacol.* 2003 July; 56(1):57-67.

Mony L, Kew J N, Gunthorpe M J, Paoletti P. Allosteric modulators of NR2B-containing NMDA receptors: molecular mechanisms and therapeutic potential. *Br J Pharmacol.* 2009 August; 157(8):1301-17.

Polinsky R J. Clinical pharmacology of rivastigmine: a new-generation acetylcholinesterase inhibitor for the treatment of Alzheimer's disease. *Clin Ther* 1998; 20:634-47.

Posadas I, López-Hernández B, Ceña V. Nicotinic receptors in neurodegeneration. *Curr Neuropharmacol.* 2013 May; 11(3):298-314.

*Remington's Pharmaceutical Sciences*, Sixteenth Edition, E. W. Martin, Mack Publishing Co., Easton, Pa., 1980

*Remington: The Science and Practice of Pharmacy*, 21st Edition, Lippincott Williams & Wilkins, 2005

Saitoh K, Manabe T, Honda H, Irino O. Effects of ifenprodil glucuronide derivative on platelet aggregation and vasocontraction. *Jpn J Pharmacol.* 1987 July; 44(3):355-7.

Schepmann D, Frehland B, Lehmkuhl K, Tewes B, Wünsch B. Development of a selective competitive receptor binding assay for the determination of the affinity to NR2B containing NMDA receptors. *Pharm Biomed Anal.* 2010 Nov. 2; 53(3):603-8.

Spencer C M, Noble S. Rivastigmine. A review of its use in Alzheimer's disease. *Drugs Aging* 1998; 13:391-411.

United States Food and Drug Administration, website: www.fda.gov. US FDA NDA Applic. No. 20-823. Clinical pharmacology and biopharmaceutics review(s). Rivastigmine tartrate capsules. p.vii, p.xi., p.xiv. File accessed from Drugs@FDA on 14 Sep. 2015.

United States Food and Drug Administration, website: www.fda.gov. US FDA NDA Applic. No. 22-083. Clinical pharmacology and biopharmaceutics review(s). Part 1. Rivastigmine transdermal patch. p.87. File accessed from Drugs @FDA on 14 Sep. 2015.

Williams A C, Barry B W. Terpenes and the lipid-protein-partitioning theory of skin penetration enhancement. *Pharm Res.* 1991 January; 8(1):17-24.

Winblad B, Cummings J, Andreasen N, Grossberg G, Onofrj M, Sadowsky C, Zechner S, Nagel J, Lane R. A six-month double-blind, randomized, placebo-controlled study of a transdermal patch in Alzheimer's disease—rivastigmine patch versus capsule. *Int J Geriatr Psychiatry* 2007; 22:456-67.

Zawertailo L A, Tyndale R F, Busto U, Sellers E M. Effect of metabolic blockade on the psychoactive effects of dextromethorphan. *Hum Psychopharmacol.* 2010 January; 25(1):71-9.

Zawertailo L A. Author's response to Miller S C: Dextromethorphan to dextrorphan: a pathway towards abuse liability. *Hum Psychopharmacol.* 2011 January; 26(1):91.

What is claimed is:

1. A sustained-release aqueous intranasal formulation consisting of:
   rivastigmine tartrate in an amount of from about 0.5% to about 15% by weight of the total formulation;
   citric acid monohydrate in an amount to provide the formulation with a pH in the range of about 3 to 6;
   polyvinyl pyrrolidone in an amount selected to improve adherence of the formulation to the nasal mucosa without adversely affecting administration of the formulation as an intranasal spray, said amount being from about 0.1% to about 2% by weight of the total formulation;
   ethanol;
   benzyl alcohol;
   l-carveol; and
   water.

2. An aqueous formulation according to claim 1 wherein the pH modifying agent is present in an amount of from about 0.01% to about 2% by weight of the total formulation.

3. A method of treating a neurodegenerative disease in a mammal, comprising administering an intranasal formulation according to claim 1 to a mammal in need thereof, wherein the neurodegenerative disease is selected from Alzheimer's disease, Parkinson's disease and cognitive dysfunction syndrome.

4. The method according to claim 3 wherein the absolute bioavailability (F) of rivastigmine is equivalent to at least 60%.

5. The method according to claim 3, wherein the rivastigmine plasma concentration ($C_{max}$) of the mammal is at least about 5000 pg/mL.

6. The method according to claim 3, wherein the therapeutic rivastigmine plasma concentration ($C_{max}$) of the mammal is in the range of about 2000 pg/mL to about 20,000 pg/mL.

7. The method according to claim 5 wherein the therapeutic rivastigmine plasma concentration is maintained for a duration of at least 4 hours ($T_{maint}$).

8. The method according to claim 3 wherein the intranasal administration is associated with a reduced incidence of side effects.

* * * * *